United States Patent
Liu et al.

(10) Patent No.: US 11,946,055 B2
(45) Date of Patent: Apr. 2, 2024

(54) PROTEIN ENGINEERING VIA ERROR-PRONE ORTHOGONAL REPLICATION AND YEAST SURFACE DISPLAY

(71) Applicants: The Regents of the University of California, Oakland, CA (US); President and Fellows of Harvard College, Cambridge, MA (US)

(72) Inventors: Chang C. Liu, Irvine, CA (US); Alon Wellner, Irvine, CA (US); Ziwei Zhong, Irvine, CA (US); Arjun Ravikumar, Irvine, CA (US); Andrew Kruse, Boston, MA (US); Conor Thomas McMahon, Brighton, MA (US)

(73) Assignees: The Regents of the University of California, Oakland, CA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/546,515

(22) Filed: Dec. 9, 2021

(65) Prior Publication Data
US 2022/0195442 A1     Jun. 23, 2022

Related U.S. Application Data

(60) Provisional application No. 63/123,558, filed on Dec. 10, 2020.

(51) Int. Cl.
| | |
|---|---|
| *C12N 15/70* | (2006.01) |
| *C12N 9/12* | (2006.01) |
| *C12N 15/10* | (2006.01) |
| *C12N 15/81* | (2006.01) |

(52) U.S. Cl.
CPC ........... *C12N 15/70* (2013.01); *C12N 9/1252* (2013.01); *C12N 15/102* (2013.01); *C12N 15/1058* (2013.01); *C12N 15/81* (2013.01); *C07K 2317/569* (2013.01)

(58) Field of Classification Search
CPC .... C12N 15/70; C12N 9/1252; C12N 15/102; C12N 15/1058; C12N 15/81; C07K 2317/569; C07K 2317/14; C07K 2317/622; C07K 16/00; C07K 16/44
See application file for complete search history.

(56) References Cited

U.S. PATENT DOCUMENTS 8,629,244 B2 * 1/2014 Kolkman ................ A61P 31/00
                                                          530/391.1

OTHER PUBLICATIONS

Wingler, Laura M., et al. "Distinctive activation mechanism for angiotensin receptor revealed by a synthetic nanobody." Cell 176.3 (2019): 479-490 (Year: 2019).*

Ravikumar, Arjun, Adrian Arrieta, and Chang C. Liu. "An orthogonal DNA replication system in yeast." Nature chemical biology 10.3 (2014): 175-177 (Year: 2014).*

* cited by examiner

*Primary Examiner* — Nancy J Leith
*Assistant Examiner* — Kyle Thomas Rega
(74) *Attorney, Agent, or Firm* — Suzannah K. Sundby, Esq.; Canady + Lortz LLP

(57) ABSTRACT

Disclosed herein are methods, compositions, and kits for engineering proteins using error-prone orthogonal replication (epOrthoRep) and yeast surface display (YSD).

12 Claims, 15 Drawing Sheets

Specification includes a Sequence Listing.

```
AT110 (Parental Sequence)        1    QVQLQESGGGLVQAGGSLRLSCAASGNIFDADIMGWYRQAPGKERELVASITDGGSTNYA      60
AT1011 (Prior Art epPCR)         1    QVQLQESGGGLVQAGGSLRLSCAASGNIFDVDIMGWYRQAPGKERELVASITDGGSTDIA      60
Invention (epOrthoRep + YSD)     1    QVQLQESGGGLVQAGGSLRLSCAASGNIFDADIMGWYRQAPGKECELVASITDGGSTNYA      60

AT110 (Parental Sequence)       61    DSVKGRFTISRDNAKNTVYLQMNSLKPEDTAVYYCAAIAYPDIPTYFDYDSDYFYWGQGT     120
AT1011 (Prior Art epPCR)        61    DSVKGRFTISRDNAKNTVYLQMNSLKPEDTAVYYCAAVAYPDIFTYFDYDSDNFYWGQGT     120
Invention (epOrthoRep + YSD)    61    DSVKGHFTISRDNAKNTVYLQMNSLKPEDTAVYYCAAVAYPDIPTYFDYDSDHFYWGQGT     120

AT110 (Parental Sequence)      121    QVTVSSS
AT1011 (Prior Art epPCR)       121    QVTVSSS
Invention (epOrthoRep + YSD)   121    QVTVSSS
```

Figure 10

Characteristics and Activities of SARS-CoV-2 Nanobodies

| Nb Name[a] | MW (single Nb) | MW (Fc fusion) | AHEAD cycle | Mutations (synonymous mutations not shown) | Affinity (nM) | Affinity Method | $k_{on}$ ($M^{-1}$ $s^{-1}$) | $k_{off}$ ($s^{-1}$) | Pseudovirus neutralization potency $IC_{50}$ (mg/mL) - Fc fusion | Pseudovirus neutralization potency $IC_{50}$ (nM) - Fc fusion | Competition against ACE2 binding (Strong, Moderate, None)[b] | Affinity measurement notes | Pseudovirus neutralization notes |
|---|---|---|---|---|---|---|---|---|---|---|---|---|---|
| RBD1 | 12681 | 76476 | 0 | wt | 1400 | SPR kinetic | 15800 | 0.0221 | 3.76 | 49.17 | N.D. | | |
| RBD1i1 | 12650 | 76414 | 4 | E46K, T100A | 48.1 | SPR kinetic | 47700 | 0.002297 | 0.18 | 2.36 | Strong | | |
| RBD1i13 | 12578 | 76270 | 7 | E44G, E46K, K86E, T100A | 32.2 | SPR kinetic | 67160 | 0.0021595 | 0.05 | 0.66 | Strong | | |
| RBD3 | 12954 | 77022 | 0 | wt | 6000 | SPR equilibrium | N/A | N/A | >26 | >337.56 | N.D. | Saturation not reached | Saturation not reached |
| RBD3i2 | 12919 | 76952 | 4 | V2A, Y58R | 128 | SPR equilibrium | N/A | N/A | 5.52 | 71.73 | N.D. | | |
| RBD3i17 | 12859 | 76832 | 8 | V2A, Y58R, Y59C | 230 | SPR equilibrium | N/A | N/A | 0.116 | 1.51 | N.D. | | |
| RBD6 | 13333 | 77780 | 0 | wt | 990 | SPR kinetic | 9011 | 0.008917 | 0.25 | 3.21 | N.D. | | |

Figure 15

| | | | | | | | | | | | |
|---|---|---|---|---|---|---|---|---|---|---|---|
| RBD6id | 13385 | 77884 | 3 | S21N, S25N, D61I | 263 | SPR kinetic | 10300 | 0.002711 | 0.056 | 0.72 | Moderate | |
| RBD6i10 | 13370 | 77854 | 6 | S21N, E46K, D61V, S121N | 597 | SPR kinetic | 9500 | 0.005675 | 1.14 | 14.64 | N.D. | |
| RBD6i13 | 13312 | 77738 | 9 | S21N, E46K, D61V, D103G, S121N | 558 | SPR equilibrium | N/A | N/A | >28 | >359 | Moderate | Saturation not reached |
| RBD7 | 13199 | 77512 | 0 | wt | 2210 | SPR equilibrium | N/A | N/A | >300 | >3870 | N.D. | Saturation not reached |
| RBD7i12 | 13139 | 77392 | 6 | Y104C | 2590 | SPR equilibrium | N/A | N/A | 7.37 | 95.23 | N.D. | Saturation not reached |
| RBD7i13 | 13138 | 77390 | 6 | E46K, Y104C | 658.75 | SPR equilibrium | N/A | N/A | >63 | >814 | N.D. | |
| RBD8 | 12780 | 76674 | 0 | wt | 80.8 | On-yeast EC$_{50}$ | N/A | N/A | N.D. | N.D. | N.D. | |
| RBD8i1 | 12720 | 76554 | 4 | F29S | 35.4 | On-yeast EC$_{50}$ | N/A | N/A | N.D. | N.D. | N.D. | |
| RBD9 | 13841 | 78796 | 0 | wt | 131 | On-yeast EC$_{50}$ | N/A | N/A | N.D. | N.D. | N.D. | |
| RBD9i10 | 13754 | 78622 | 4 | T55A, D61G, N83D | 15.2 | On-yeast EC$_{50}$ | N/A | N/A | N.D. | N.D. | N.D. | |

Figure 15 cont.

| | | | | | | | | |
|---|---|---|---|---|---|---|---|---|
| RBD10 | 13616 | 78346 | 0 | wt | 417 | 13200 | 0.005521 | >45 | >574 | N.D. | Saturation not reached |
| RBD10i10 | 13455 | 78024 | 4 | E44G, E46K, S55G, D61G | 2.14 | SPR kinetic | 153966.67 | 0.00 | 0.19 | 2.44 | None | |
| RBD10i14 | 13453 | 78020 | 7 | E44G, E46K, M34V, D61G | 0.722 | SPR kinetic | 167200 | 0.0001182 | 0.42 | 5.38 | N.D. | |
| RBD11 | 12853 | 76820 | 0 | wt | 2420 | SPR equilibrium | N/A | N/A | >37 | >481 | N.D. | Saturation not reached |
| RBD11i12 | 12837 | 76788 | 4 | E44G, H105Y, G109S | 316 | SPR equilibrium | N/A | N/A | 0.04 | 0.52 | Moderate | | a Nanobody (Nb) naming follows the convention of XYiZ where X = Target, Y= Parent Clone Number, and Z = Affinity Matured Clone Number (or Letter)
b Strong indicates no change in response upon addition of ACE2 to Nb-bound RBD, moderate indicates some change in response upon addition of ACE2 to Nb-bound RBD, none indicates a typical association response profile upon addition of ACE2 to Nb-bound RBD.

Figure 15 cont.

PROTEIN ENGINEERING VIA ERROR-PRONE ORTHOGONAL REPLICATION AND YEAST SURFACE DISPLAY

CROSS-REFERENCE TO RELATED APPLICATIONS

This application claims the benefit of U.S. Patent Application No. 63/123,558, filed Dec. 10, 2020, which is herein incorporated by reference in its entirety.

ACKNOWLEDGEMENT OF GOVERNMENT SUPPORT

This invention was made with Government support under Grant No. 1DP2GM119163-01, awarded by the National Institutes of Health. The Government has certain rights in the invention.

REFERENCE TO A SEQUENCE LISTING SUBMITTED VIA EFS-WEB

The content of the ASCII text file of the sequence listing named "20211209_034044_212US1_ST25" which is 114,764 bytes in size was created on Dec. 9, 2021 and electronically submitted via EFS-Web herewith the application is incorporated herein by reference in its entirety.

BACKGROUND OF THE INVENTION

1. Field of the Invention

Protein engineering using error-prone orthogonal replication and yeast surface display.

2. Description of the Related Art

Designer proteins, including affinity reagents (e.g., antibodies and fragments thereof) and enzymes, are important for biomedical research, diagnostics, therapeutics, and industrial biotechnology. Because of the limitations of the currently available tools for designing and screening proteins, the development of designer proteins is slow, costly, and often fails to result in a protein with the desired characteristics and function.

Yeast surface display (YSD) is popular tool for affinity reagent discovery, library screening, and directed evolution of protein binders. YSD is facilitated by the expression of recombinant proteins onto the cell wall of *Saccharomyces cerevisiae*. YSD allows eukaryotic expression of a heterologous target protein whereby folding, modification, and translocation of the protein occurs prior to its display on the surface. YSD offers versatility in screening, as it supports the enrichment of proteins that bind desired targets by fluorescence activated cell sorting (FACS), which requires cells as the entity being sorted and is therefore not compatible with phage display. FACS allows precise gating to enrich binders with specific properties and is capable of preventing the enrichment of avidity-based effects in binding.

YSD may be used to express and screen combinatorial libraries. A notable example is a $10^9$-member nonimmune short chain variable fragment (scFv) library comprised of shuffled heavy and light chain genes mimicking the natural germline diversity of human B-lymphocytes. The scFv libraries can then be used to isolate scFvs against several diverse small molecules and protein targets of interest. In cases where biased libraries toward particular antigens are desired, partial-immune and immune libraries of scFv are created by cloning B lymphocyte cDNA from immunized animals or from human healthy individuals who display higher than average titers of antibody against a particular antigen. YSD may be used for antibody affinity maturation. Because each yeast cell is capable of displaying 100,000 scFv molecules on average, yeast cells displaying labeled scFvs (e.g., fluorescein labeled scFvs) can be detected and precisely quantified by flow cytometry.

A major drawback of YSD, however, is the low transformation efficiency of *Saccharomyces cerevisiae* that severely bottlenecks population size during successive rounds of directed evolution. In addition, for challenging affinity maturation campaigns, between each round, the library of YSD proteins needs to be re-randomized through a process involving DNA extraction; error-prone PCR, gene shuffling, or other in vitro diversification techniques; cloning and plasmid preparation; and transformation. This cycle is highly onerous and time consuming thus limiting the number of rounds and consequently the number of mutational steps that are needed to achieve strong binding affinities (low nanomolar ranges). The labor-intensive nature of this cycle also limits the scale and number of YSD experiments experimenters can carry out, meaning that one researcher can only carry out a handful of affinity maturation experiments at a time, making it difficult to generate good protein binders to multiple different targets, multiple different epitopes of the same target, or multiple different binders to the same epitope, useful for maximizing the downstream chance of success of applications including development of antibodies into drugs.

Error-prone orthogonal replication has been used to direct continuous evolution at mutation rates above genomic error thresholds. Orthogonal replication generally involves replication of a heterologous DNA polymerase/plasmid pair that is orthogonal to host replication such that the orthogonal DNA polymerase (DNAP) replicates only the orthogonal plasmid, e.g., a P1 plasmid, and not the host genome. The P1 plasmid is a cytosolic plasmid whose replication is driven by an orthogonal DNA polymerase (DNAP). The use of error prone DNAPs result in high mutation rates (e.g., >100,000-fold higher than host genomic mutation rates) such that only the gene(s) of interest on the P1 plasmid are rapidly mutated. While, error-prone orthogonal replication has been used in yeast cells, its use has been limited to genes encoding intracellular proteins.

SUMMARY OF THE INVENTION

In some embodiments, the present invention is directed to a P1 plasmid comprising a constitutively active P1 promoter, a secretory leader sequence, and an attachment sequence. In some embodiments, the P1 plasmid further comprises a polyA tail, a self-cleaving ribozyme sequence, or both a polyA tail, a self-cleaving ribozyme sequence. In some embodiments, the constitutively active P1 promoter comprises one or more TATA sequences. In some embodiments, the constitutively active P1 promoter is SEQ ID NO: 2 (p10B2) or SEQ ID NO: 7 (pGA). In some embodiments, the secretory leader sequence encodes SEQ ID NO: 6 (app8). In some embodiments, the secretory leader sequence encodes SEQ ID NO: 11 (app8il). In some embodiments, the attachment sequence encodes SEQ ID NO: 1 (AGA2). In some embodiments, the polyA tail comprises at least 50, preferably at least 60, more preferably at least 70, and even more preferably at least 75 adenosine bases. In some embodiments, the polyA tail comprises 75 adenosine bases. In some embodiments, the self-cleaving ribozyme sequence is a Hammerhead ribozyme known in the art such as that described in Hammann et al. (2012) RNA 18(5):871-885, which is herein incorporated by reference in its entirety. In some embodiments, the self-cleaving ribozyme sequence encodes SEQ ID NO: 4 (Hammerhead ribozyme). In some embodiments, the P1 plasmid comprises a selection marker, e.g., Trp1. In some embodiments, the P1 plasmid comprises a tag, e.g., an HA tag, for detecting protein expression. In some embodiments, the P1 plasmid comprises a parental sequence of interest or a backbone sequence, e.g., a restriction enzyme site, into which the parental sequence of interest may be inserted. In some embodiments, the parental sequence of interest or the backbone sequence having the restriction enzyme site, is located between the secretory leader sequence and the tag. In some embodiments, the backbone sequence comprises SEQ ID NO: 10, wherein the region of Xaa's is any CDR3 sequence of interest. In some embodiments, the P1 plasmid is a P1 expression plasmid. In some embodiments, the P1 plasmid is a P1 integration plasmid. In some embodiments, the P1 plasmid comprises terminal proteins flanking a wildtype DNA polymerase that is endogenous to the terminal proteins and a selection marker, e.g., Met15. In some embodiments, the P1 plasmid comprises SEQ ID NO: 8.

In some embodiments, the present invention is directed to a yeast host cell comprising a P1 plasmid according described herein. In some embodiments, the yeast host cell comprises an error prone DNA polymerase that replicates the P1 plasmid at an error rate above the average normal genomic error rate of the yeast host cell, and one or more or all P2 components for orthogonal replication the P1 plasmid.

In some embodiments, the present invention is directed to a method of engineering a protein having a desired characteristic, which comprises subjecting a yeast host cell containing a P1 plasmid as described herein to error prone orthogonal replication (epOrthoRep) and then selecting yeast cells expressing, on their cell surface, the protein having the desired characteristic.

In some embodiments, the present invention is directed to a method of engineering a protein having a desired characteristic, which comprises identifying the one or more mutations in a given protein that confers the desired characteristic and recombinantly or synthetically modifying the given protein to have one or more of the identified mutations.

In some embodiments, the present invention is directed to a kit comprising a P1 plasmid as described herein packaged together with one or more reagents or devices for transducing a yeast cell therewith. In some embodiments, the P1 plasmid is packaged together with a yeast host cell comprising one or more or all P2 components for orthogonal replication of the P1 plasmid. In some embodiments, the yeast host cell is packaged together with one or more reagents or devices for culturing and/or transducing the yeast host cell.

In some embodiments, the present invention is directed to a nanobody selected from the group consisting of SEQ ID NO: 24, SEQ ID NO: 25, SEQ ID NO: 27, SEQ ID NO: 28, SEQ ID NO: 30, SEQ ID NO: 31, SEQ ID NO: 32, SEQ ID NO: 34, SEQ ID NO: 35, SEQ ID NO: 37, SEQ ID NO: 39, SEQ ID NO: 41, SEQ ID NO: 42, SEQ ID NO: 44, SEQ ID NO: 46, SEQ ID NO: 47, SEQ ID NO: 49, SEQ ID NO: 50, SEQ ID NO: 52, SEQ ID NO: 53, SEQ ID NO: 54, SEQ ID NO: 56, SEQ ID NO: 57, SEQ ID NO: 59, SEQ ID NO: 60, and SEQ ID NO: 62.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein:

FIG. 2 schematically shows the detection of the ScFv fragment bound to the yeast surface cell. As shown, the antigen binding protein (ScFV) is fused at its N-terminus.

FIG. 3 summarizes the results of fluorescein binding experiments evidencing the surface display of 4M5.3 encoded from a P1 expression plasmid and its fluorescein binding activity (black curve, third curve having arrow pointing thereto). Red curve (first curve) corresponds to no display control. Blue curve (fourth curve) corresponds to display of 4M5.3 from a nuclear CEN/ARS plasmid driven by the inducible pGAL promoter instead of display from the P1 expression plasmid. Green curve (second curve) corresponds to display of a lower-affinity anti-fluorescein scFv, also encoded on a nuclear CEN/ARS plasmid driven by the inducible pGAL promoter instead of display from the P1 expression plasmid.

Affinity ($EC_{50}$) of each AT110 mutant for AT1R was determined by measuring binding to each concentration of AT1R-angiotensin II complex (X-axis) in a single replicate and fitting the resulting binding curve.

Figure 8:
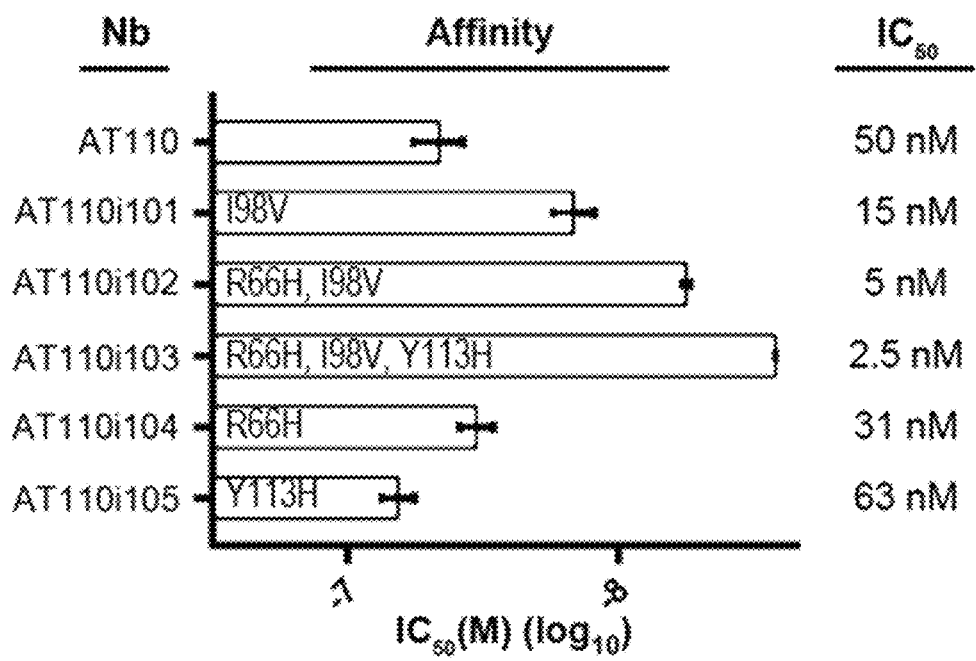

FIG. 8 shows the activities of the AT110 mutants with their accumulated mutations from artificial evolution-mutations leading to enhanced affinity for AT1R. Error bars represent the SEM from three independent experiments performed as single replicates.

Figure 1:
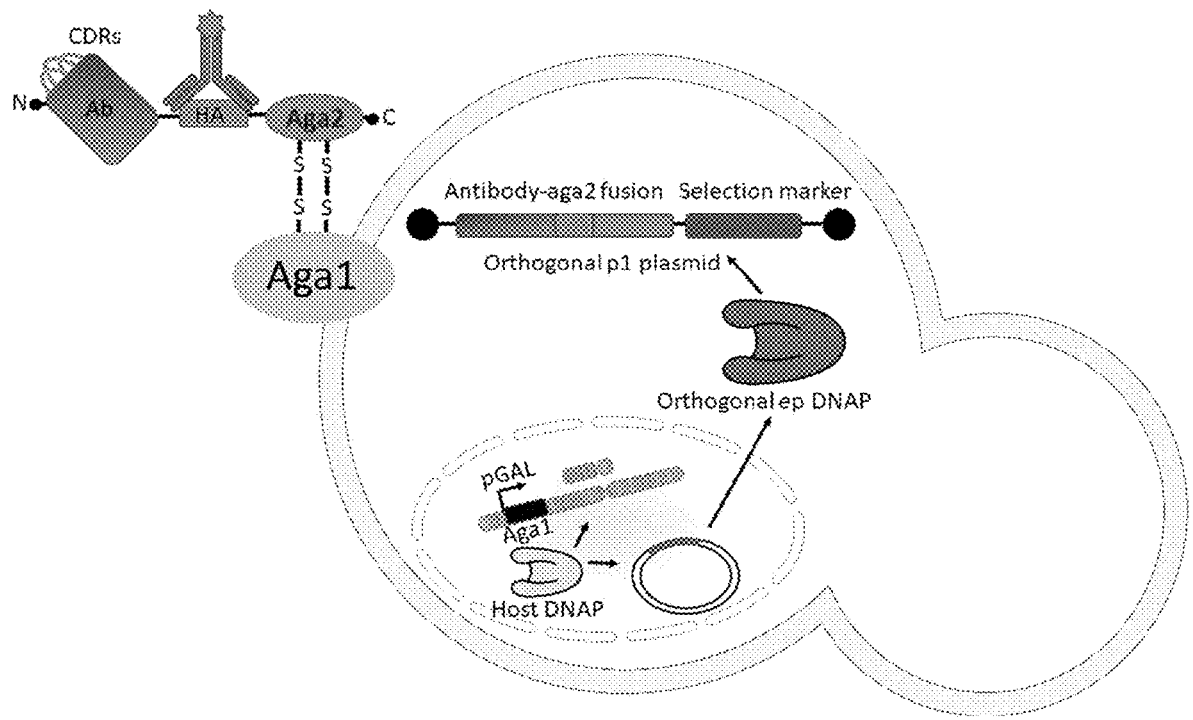
FIG. 1 schematically illustrates YSD of an antigen binding protein expressed using orthogonal replication. As shown, the antigen binding protein (Ab) is fused at its C-terminus.
Figure 2:
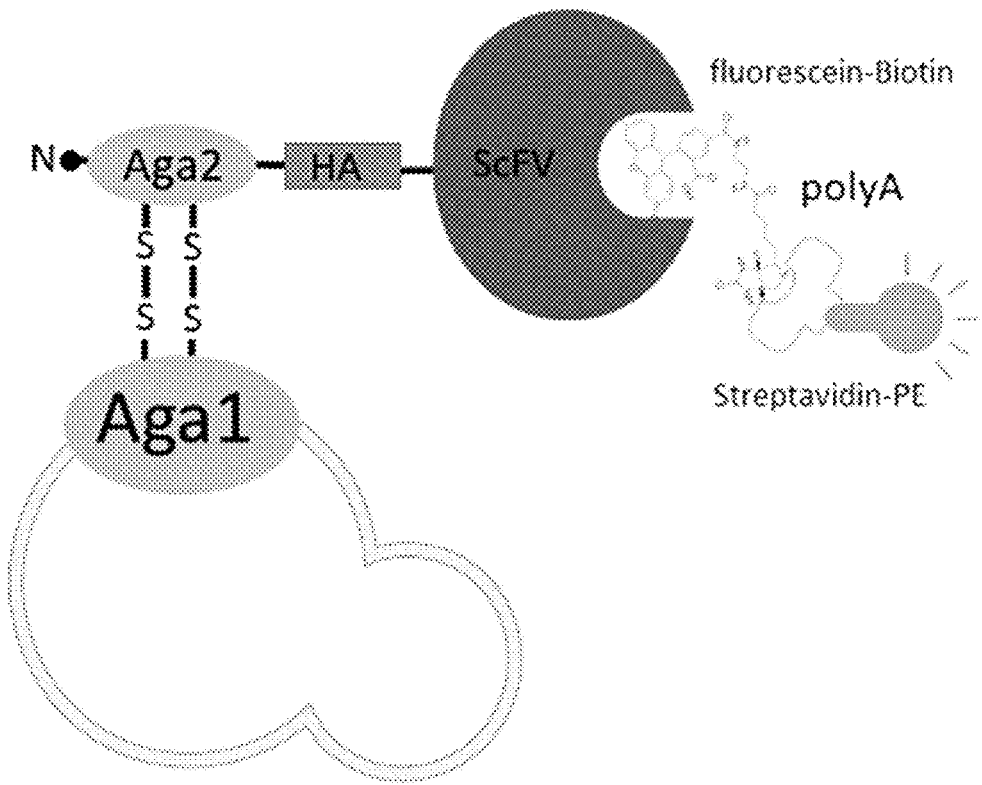
FIG. 2 to FIG. 3: Expression of 4M5.3 from a P1 expression plasmid having a 3'polyA(75A) and a 10B2 promoter. The exemplified parental sequence was an ScFv fragment, 4M5.3, which binds fluorescein (Boder & Wittrup (1997)) fused to AGA2.
Figure 3:
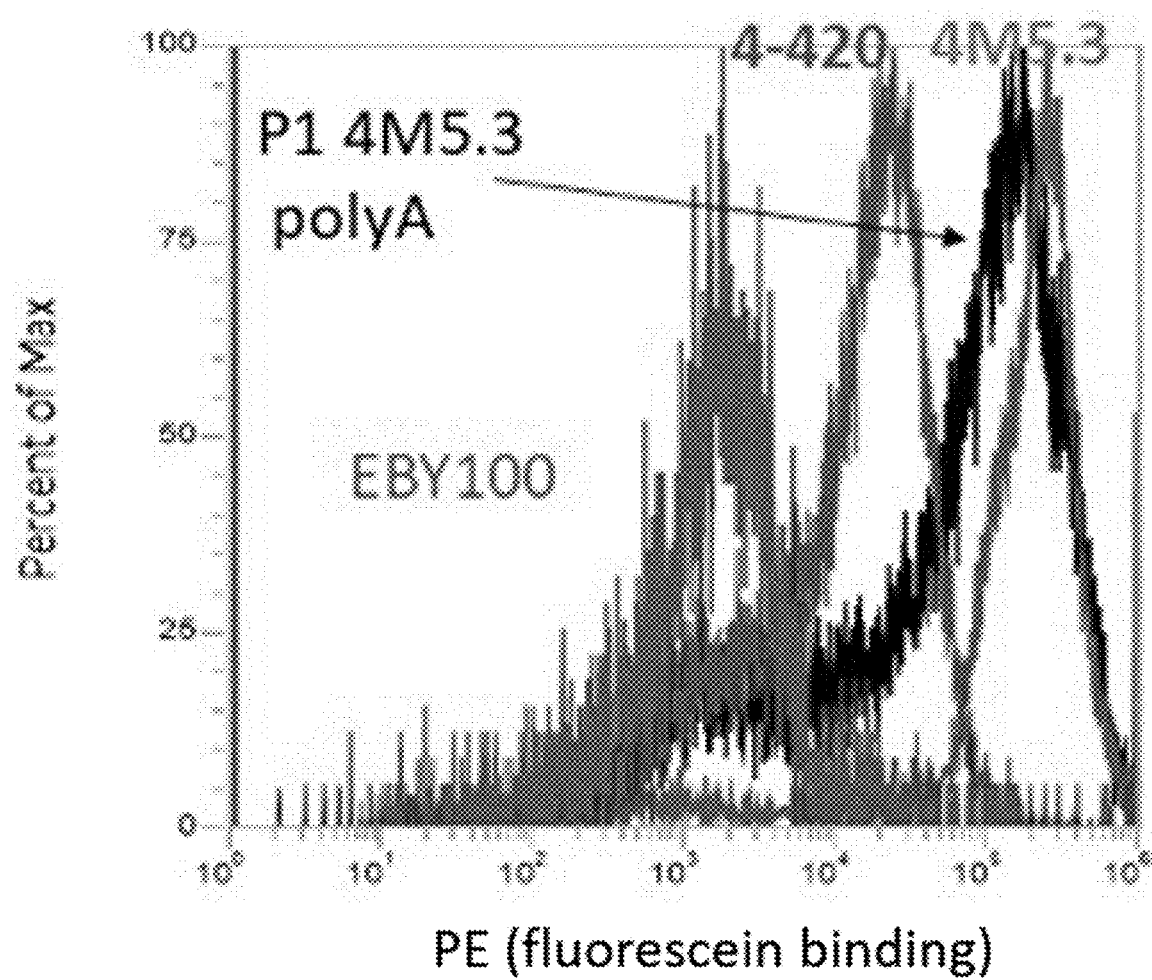
Figure 9:
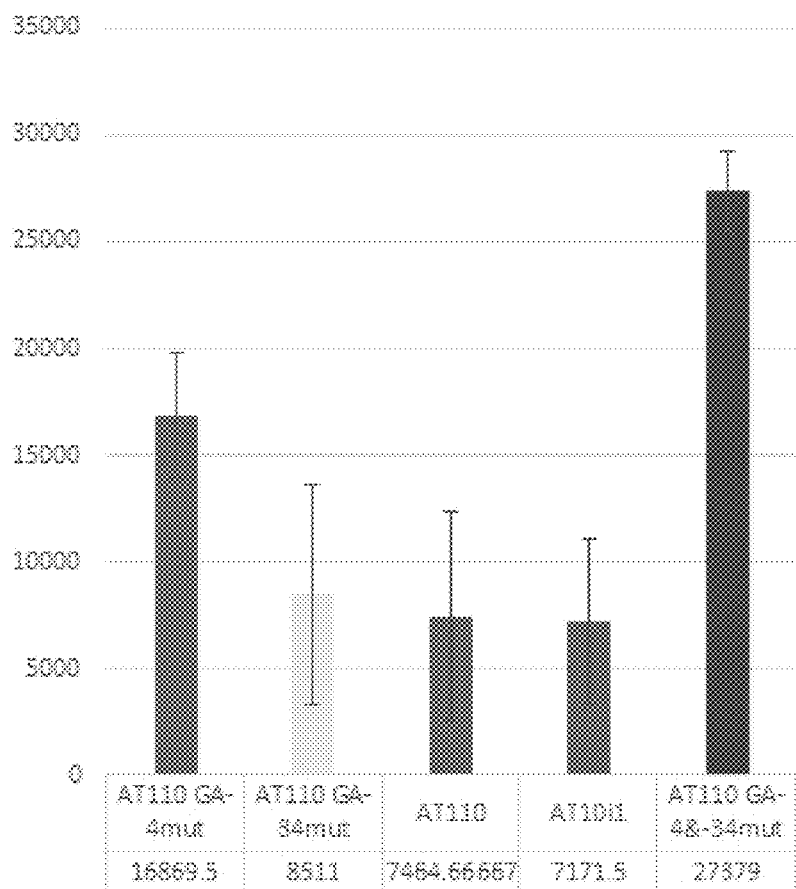

FIG. 9 shows that the pGA promoter (red bar, 5th bar) drives the expression of AT110 much more than previous systems (blue bars, 3rd and 4th bars) allowing for greater display efficiency. AT10il is a nanobody that was designed based on AT110 using affinity maturation methods in the art. See Wingler L M, et al. (2019).

FIG. 10 is a sequence alignment showing the mutations resulting from artificial evolution of AT110 (parental sequence, SEQ ID NO: 4) using error-prone PCR methods in the prior art (AT10il, SEQ ID NO: 65) and epOrthoRep combined with YSD as disclosed herein (Invention, SEQ ID NO: 66).

FIG. 11 schematically shows the CEN/ARS plasmid that encodes an error prone TP-DNAP1 as exemplified herein. Other plasmids and error prone TP-DNAP1s in the art may be used accordingly. See, for example, WO 2019/079775, which is herein incorporated by reference in its entirety.

FIG. 12 schematically shows an exemplary P1 integration plasmid tailored for nanobody library construction.

FIG. 13 schematically shows a P1 integration plasmid for "optimized epOrthoRep" as described herein.

FIG. 14 shows the affinities ($EC_{50}$) of evolved nanobodies using optimized epOrthoRep. Left: Binding of Nb.b201 mutants by each concentration of HSA was measured in replicate (n=3, error bars represent±s.d.) and $EC_{50}$s were determined by fitting each binding curve. Right: Binding of Lag42 mutants by each concentration of GFP was measured in replicate (n=3, error bars represent±s.d.) and EC50s were determined by fitting each binding curve.

FIG. 15 is a graph summarizing the characteristics and activities of the SARS-CoV-2 nanobodies provided herein.

FIG. 16 is a graph showing the affinity ($EC_{50}$) of NbG1i1, an anti-GFP nanobody that was de novo designed, compared to its parent, NbG1. Binding of yeast-displayed nanobodies by each concentration of GFP was determined in replicate (n=3, error bars represent±s.d.) and $EC_{50}$'s were determined by fitting each binding curve.

DETAILED DESCRIPTION OF THE INVENTION

Provided herein are methods, compositions, and kits for engineering proteins using error-prone orthogonal replication (epOrthoRep) and yeast surface display (YSD). The combination of epOrthoRep and surface display in yeast cells allows the continuous evolution of proteins, which may be readily screened and/or enriched for proteins having desired characteristics.

P1 and P2 linear cytosolic plasmids are stably propagated in the yeast strain, F102. Use of yeast strains such as F102 (ATCC 200585) and epOrthoRep results in intracellularly expressed proteins. In order for surface display of proteins, the proteins must be transported to the exterior surface of the yeast cells by way of a signal peptide and then attached thereto by way of an attachment sequence that has a binding partner on the surface. Prior art yeast host cells used for YSD, such as EBY100, do not contain P1 plasmids and other components that allow epOrthoRep and prior art yeast host cells used for epOrthoRep do not contain the components that allow YSD. However, as described herein, simply combining the prior art systems and architectures of epOrthoRep and YSD fails to result in detectable levels of surface displayed proteins.

Therefore, as disclosed herein, modifications to the orthogonal replication system described Ravikumar A, et al. (2014) Nat Chemical Biology 10:175-177 and Ravikumar A, et al. (2018) Cell 175:1946-1957 were made to result in surface display of mutant proteins produced by orthogonal replication. Once displayed on the yeast host cell surface, the mutant proteins were subjected to FACS-based enrichment for mutant proteins exhibiting a desired characteristic (e.g., improved binding of given target). After a few rounds of enrichment, mutant proteins having the desired characteristic were obtained. Thus, the methods, compositions, and kits described herein may be used to engineer proteins having one or more desired characteristics without the need for in vitro mutagenesis and numerous yeast cell transformations (e.g., one transformation per mutant).

Yeast Surface Display of Proteins from Error-Prone Orthogonal Replication

Because YSD systems use high-strength induced expression of genes for cell surface display whereas known orthogonal replication systems do not support high-strength expression of genes encoded on the P1 plasmid and because the process of transcription, capping, and translation of genes using orthogonal replication systems is not fully elucidated, it was unknown whether the combination of epOrthoRep and YSD would likely be successful in the surface display of continuously evolving mutant proteins.

Therefore, to determine whether proteins expressed by orthogonal replication are capable of being exported and displayed on the surface of yeast cells, prior art systems and architectures for epOrthoRep and YSD were combined. Specifically, a prior art P1 integration plasmid was modified to encode a variety of test proteins (e.g., scFvs, nanobodies, etc.) that were targeted for secretion and surface display by adding an N-terminal secretory leader sequence and an attachment sequence, the *Saccharomyces cerevisiae* agglutination factor, AGA2 (SEQ ID NO: 1). The P1 integration plasmids encoding these "AGA2-fusion proteins" were transduced into F102 (ATCC 200585) yeast cells. The F102 yeast strain is often used in the art for orthogonal replication. Upon transduction, the nucleic acid sequence encoding the AGA2-fusion proteins were integrated in the P1 plasmids of the F102 yeast cells by homologous recombination. The yeast cells having P1 plasmids encoding the AGA2-fusion proteins were fused to EBY100 yeast cells using protoplast fusion methods in the art. The EBY100 yeast strain is often used in the art for YSD.

If successfully expressed and secreted in the F102/EBY100 yeast cells, the AGA2-fusion proteins will coat the extracellular cell wall surface by virtue of disulfide bond formation with AGA1 (a GPI/β-1,6-glucan-anchored protein) and be detectable as schematically shown in FIG. 1. Unfortunately, the combination of the prior art systems and architectures epOrthoRep and YSD failed to provide levels of surface displayed proteins that could be detected by flow cytometry, even when using the strongest natural promoter for P1 genes, P2ORF10.

Therefore, the P1 integration plasmids were further modified to have a constitutively active promoter, p10B2 (SEQ ID NO: 2), and a polyA tail having 75 adenosines followed by a self-cleaving ribozyme (i.e., a Hammerhead ribozyme (SEQ ID NO: 3)). This gave a P1 expression plasmid having the constitutively active promoter, polyA tail, and self-cleaving ribozyme and resulted in detectable expression of a fluorescein binding ScFv, 4M5.3. See FIG. 2 and FIG. 3.

Engineered Evolution of Desired Proteins

To determine whether epOrthoRep and YSD may be combined and used to artificially evolve a protein having a desired characteristic, a human G-protein coupled receptor (GPCR) binding nanobody, AT110, was used as a parental sequence. AT110 was originally designed to bind the angiotensin II type 1 receptor (AT1R).

The amino acid sequence of AT110 is:

(SEQ ID NO: 4)
QVQLQESGGGLVQAGGSLRLSCAASGNIFDADIMGWYRQAPGKERELVA

SITDGGSTNYADSVKGRFTISRDNAKNTVYLQMNSLKPEDTAVYYCAAI

AYPDIPTYFDYDSDYFYWGQGTQVTVSSS

The wildtype amino acid sequence of AT1R is set forth in Accession No. P30556.1.

The AT1R sequence exemplified in the experiments herein has a FLAG peptide (underlined) fused to its N-terminus as follows:

(SEQ ID NO: 5)
<u>DYKDDDDK</u>ILNSSTEDGIKRIQDDCPKAGRHNYIFVMIPTLYSIIFVVG

IFGNSLVVIVIYFYMKLKTVASVFLLNLALADLCFLLTLPLWAVYTAME

YRWPFGNYLCKIASASVSFNLYASVFLLICLSIDRYLAIVHPMKSRLRR

TMLVAKVICIIIWLLAGLASLPAIIHRNVFFIENTNITVCAFHYESQNS

TLPIGLGLIKNILGFLFPFLIILTSYTLIWKALKKAYEIQKNKPRNDDI

FKIIMAIVLFFFFSWIPHQIFTFLDVLIQLGIIRDCRIADIVDTAMPIT

ICIAYFNNCLNPLFYGFLGKKFKRYFLQLLKYIPPKAKSHSNLSTKMST

LSYRPSDNVSSSTKKPAPCFEVE

Figure 4:
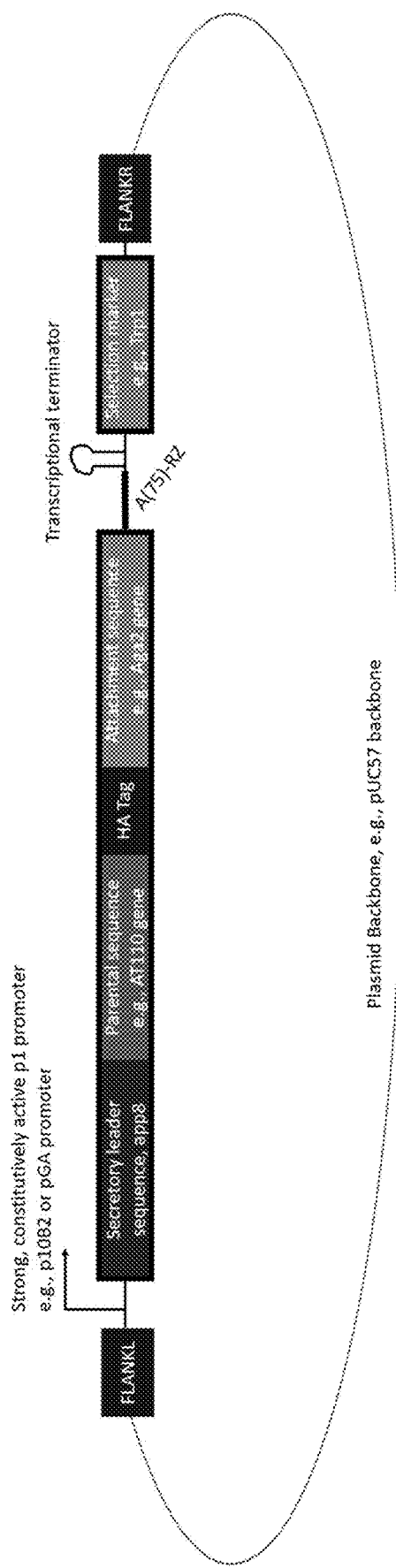
FIG. 4 schematically shows the P1 integration plasmid used for the artificial evolution of nanobody AT110. The P1 integration plasmid contains a DNA cassette comprising a strong, constitutively active promoter, e.g., 10B2, the nucleic acid sequence encoding the AT110 nanobody fused to the AGA2 gene, a genetically encoded polyA tail, and an auxotrophic selection marker for yeast transformation, e.g., Trp1, which DNA cassette was flanked by two recombination sequences ("FLANKL" and "FLANKR") that are homologous to the ends of the P1 plasmid of F102. Orientation of AGA2 can also be before or after the AT110 nanobody in the fusion protein and the location of the HA tag can vary. Trp1—an auxotrophic selection marker driven by a promoter such as p1O2, HA tag—a protein tag for detection of protein expression, p10B2 or pGA—promoters specific for expression of genes encoded on the P1 plasmid.
Figure 5:
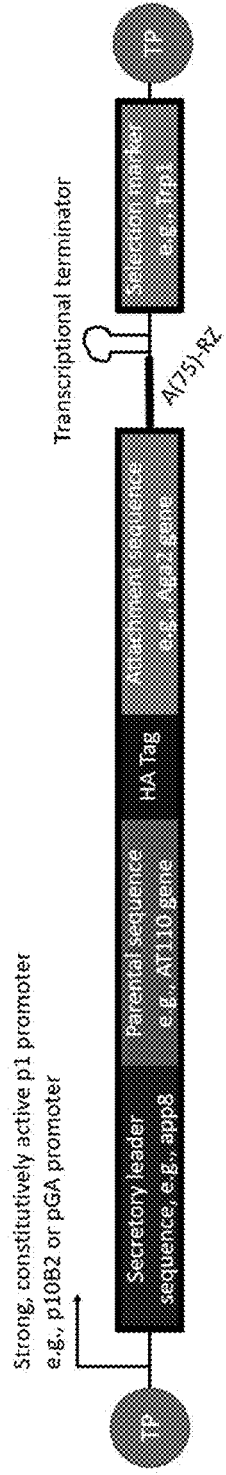
FIG. 5 schematically shows the P1 expression plasmid used for artificial evolution of AT110. TP—terminal proteins, Trp1—an auxotrophic selection marker driven by a promoter such as p102, HA tag—a protein tag for detection of protein expression, p10B2 or pGA—promoters specific for expression of genes encoded on the P1 plasmid.

The nucleic acid sequence encoding AT110 was cloned into a plasmid as a fusion with the AGA2 gene to give a P1 integration plasmid as schematically shown in FIG. 4. The P1 integration plasmid was linearized with a restriction endonuclease that targets the external regions of the homology flanks. F102 yeast cells were then transduced with the linearized P1 integration plasmid. After selection using synthetic media lacking tryptophan, correct integration of the DNA cassette encoding the AGA2-fusion protein into the P1 plasmid of F102 was confirmed in individual colonies using methods in the art. The P1 expression plasmid resulting from homologous recombination between the P1 plasmid and the linearized P1 integration plasmid is schematically shown in FIG. 5.

Yeast cells having the P1 expression plasmid were fused with EBY100 cells, which were previously transformed with a CEN/ARS plasmid encoding the error prone DNAP1, by protoplast fusion. The resulting yeast strain was cultured in media lacking histidine, uracil, leucine, and tryptophan until saturation and subsequently diluted into fresh media by a factor of 1:10,000 to allow regrowth. This was iterated several times to allow accumulation of mutations in the parental sequence as a result of epOrthoRep. After several cycles of culturing and regrowth, the yeast cells were cultured in media containing 2% galactose instead of glucose and at room temperature for 48 hours to induce AGA1 production and then contacted with the agonist-bound conformation of AT1R. Stained yeast cells, i.e., yeast cells having AT1R bound thereto were selected via FACS sorting and subjected to additional rounds of culturing, regrowth, AT1R staining, and FACS sorting as summarized in Table 1.

TABLE 1

|  | Volume of Passage | Final OD | Media | # Divisions during passage | Total # of Divisions |
|---|---|---|---|---|---|
| Starter culture | Streak from plate into 3 mL | 20.2 | GLU | <10 |  |
| Passage 1 | 50 µl into 2 L | 3.6 | GLU | 12.80 | 12.80 |
| Passage 2 | 5 mL into 500 mL | 10.8 | GAL | 8.23 | 21.03 |
| Passage 3 1 µM AT1R staining After FACS Round 1 | 2 mL into 250 mL | 10.3 | GAL | 6.90 | 27.93 |
| FACS culture | 18,218 cells in 3 mL | 13.9 | GLU | 15.08 | 43.01 |
| Passage 1 | 100 µl in 50 mL | 12.3 | GLU | 8.79 | 51.80 |
| Passage 2 | 100 µl in 50 mL | 13.1 | GLU | 9.06 | 60.86 |
| Passage 3 500 nM AT1R staining After FACS Round 2 | 100 µl in 50 mL | 13.2 | GAL | 8.98 | 69.83 |
| FACS culture | 53,116 cells in ~3 mL | 6.5 | GLU | 12.44 | 82.28 |
| Passage 1 | 100 µl in 50 mL | 15 | GLU | 10.17 | 92.45 |
| Passage 2 | 100 µl in 50 mL | 5 | GLU | 7.38 | 99.83 |
| Passage 3 500 nM AT1R staining After FACS Round 3 | 100 µl in 50 mL | 15.1 | GAL | 10.56 | 110.39 |
| FACS culture | ~25,000 cells in ~3.5 mL | 6.75 | GLU | 13.79 | 124.18 |
| Passage 1 | 100 µl in 50 mL | 15.3 | GLU | 10.15 | 134.32 |
| Passage 2 | 100 µl in 50 mL | 14.5 | GLU | 8.89 | 143.21 |
| Passage 3 | 100 µl in 50 mL | 14.9 | GLU | 9.01 | 152.22 |
| Passage 4 | 100 µl in 50 mL | 15.4 | GLU | 9.01 | 161.23 |
| Passage 5 | 100 µl in 50 mL | 18.1 | GLU | 9.20 | 170.43 |

TABLE 1-continued

|  | Volume of Passage | Final OD | Media | # Divisions during passage | Total # of Divisions |
|---|---|---|---|---|---|
| Passage 6 | 100 µl in 50 mL | 16.1 | GLU | 8.80 | 179.23 |
| Passage 7 | 100 µl in 50 mL | 3.4 | GLU | 6.72 | 185.95 |
| Passage 8 | 2.5 mL into 50 mL | 10.6 | GAL | 5.96 | 191.91 |
| 200 nM AT1R staining | | | | | |
| After FACS Round 4 | | | | | |
| FACS culture | 21,455 cells in 3 mL | 14.8 | GLU | 14.95 | 206.86 |
| Thawed aliquot from FACS | 430,000 surviving cells in 50 mL | 16.1 | GLU | 14.76 | 221.63 |
| Passage 1 | 50 µl in 50 mL | 16.1 | GLU | 9.97 | 231.59 |
| Passage 2 | 50 µl in 50 mL | 14.7 | GLU | 9.83 | 241.43 |
| Passage 3 | 50 µl in 50 mL | 15.1 | GLU | 10.00 | 251.43 |
| Passage 4 | 50 µl in 50 mL | 14.7 | GLU | 9.93 | 261.36 |
| Passage 5 | 2.5 mL into 50 mL | 12.8 | GAL | 4.12 | 265.48 |
| 150 nM AT1R staining | | | | | |
| After FACS Round 5 | | | | | |
| FACS culture | 1,704 cells in 3 mL | 13.9 | GLU | 18.70 | 284.18 |
| Passage 1 | 100 µL in 50 mL | 14.4 | GLU | 9.02 | 293.20 |
| Passage 2 | 50 µL in 50 mL | 14.2 | GLU | 9.95 | 303.15 |
| Passage 3 | 2 mL into 50 mL | 12.5 | GAL | 4.46 | 307.61 |
| 15 nM AT1R staining | | | | | |
| After FACS Round 6 | | | | | |
| FACS culture | 8,631 cells in ~3 mL | 19.5 | GLU | 16.63 | 324.24 |
| Passage 1 | 100 µl in 50 mL | 14.2 | GLU | 8.51 | 332.75 |
| Passage 2 | 100 µl in 50 mL | 16.9 | GLU | 9.22 | 341.96 |
| Passage 3 | 100 µl in 50 mL | 14.3 | GLU | 8.72 | 350.69 |
| Passage 4 | 100 µl in 40 mL | 13.8 | GLU | 8.91 | 359.60 |
| Passage 5 | 100 µl in 50 mL | 15.3 | GLU | 9.11 | 368.72 |
| Passage 6 | 2 mL in 50 mL | 15 | GAL | 4.62 | 373.33 |
| 15 nM AT1R staining | | | | | |
| After FACS Round 7 | | | | | |
| FACS culture | 3,322 cells in 3.5 mL | 15.9 | GLU | 17.72 | 391.05 |
| Passage 1 | 50 µl in 50 mL | 13.8 | GLU | 9.76 | 400.81 |
| Passage 2 | 50 µl in 50 mL | 13.8 | GLU | 9.97 | 410.78 |
| Passage 3 | 2.5 mL into 50 mL | 4.8 | GAL | 2.80 | 413.58 |
| 15 nM AT1R staining | | | | | |

*After staining, a 3-hour incubation at 37° C. for selection of lower off-rate

Figure 6:
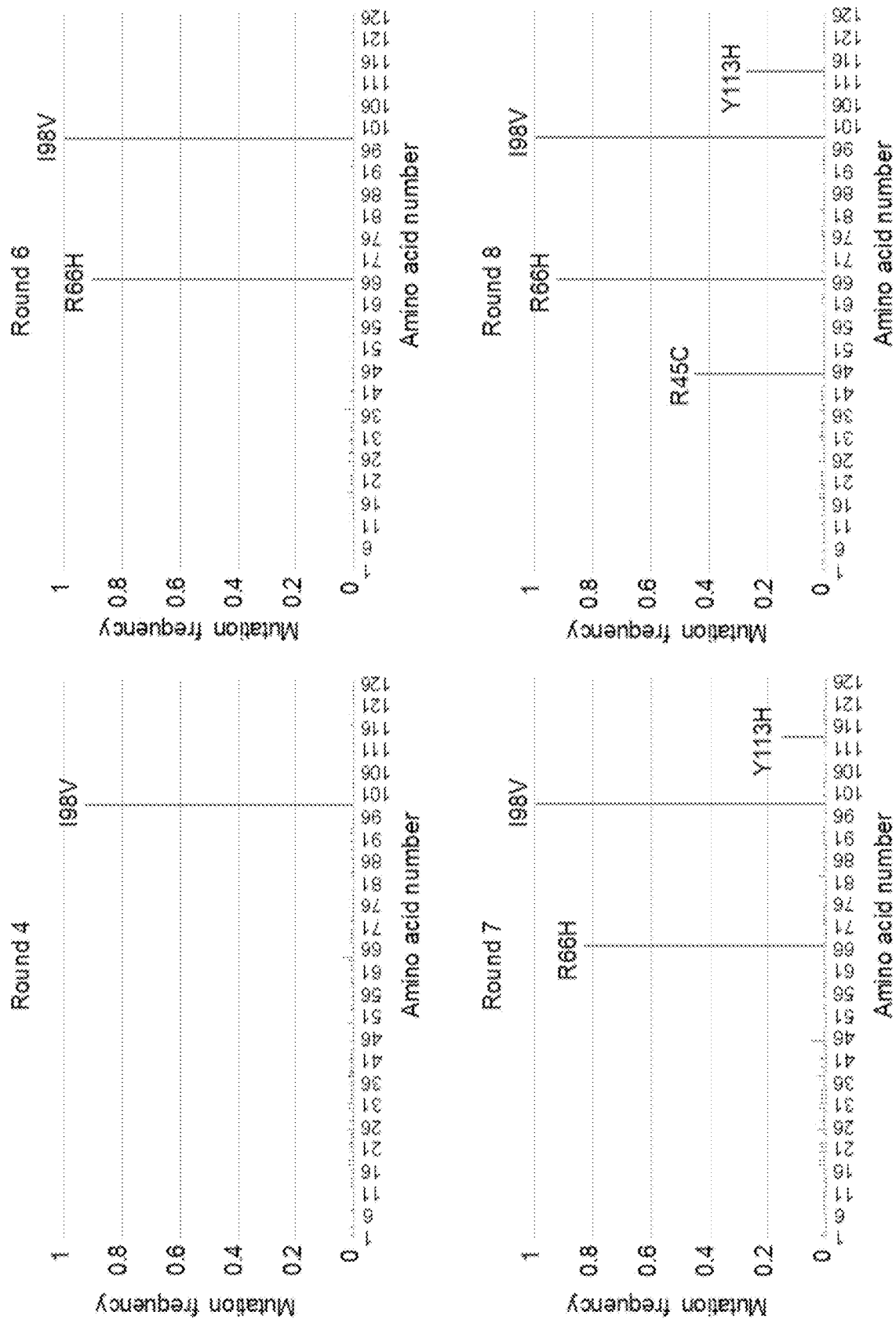
FIG. 6 summarizes the dominant mutations obtained by artificial evolution of AT110 that result in higher affinity towards ATIR after the indicated rounds of sequence diversification and selection.

Following 8 rounds of sequence diversification (i.e., one round of sequence diversification comprises a set (plurality) of culture passaging cycles prior to enrichment by, e.g., FACS selection) and FACS selection whereby the stringency of selection was increased by successively lowering the AT1R concentration in each FACS selection round, the P1 expression plasmid evolved to express proteins exhibiting a higher affinity for AT1R as compared to the original parental sequence. Next-generation sequencing analysis of the P1 expression plasmids in the yeast cells after each round of sequence diversification indicate that the overall number of mutations increased and mutations encoding specific amino acid modifications (e.g., substitutions) were increasingly selected for (or against) as exemplified in FIG. 6.

After FACS Round 7, and a 3-hour incubation at 37° C., the dominant mutations, R45C, R66H, I98V, and Y113H, and combinations of one or more, were subjected to functional assays to determine their role in conferring the desired characteristic, i.e., increased affinity for AT1R.

Figure 7:
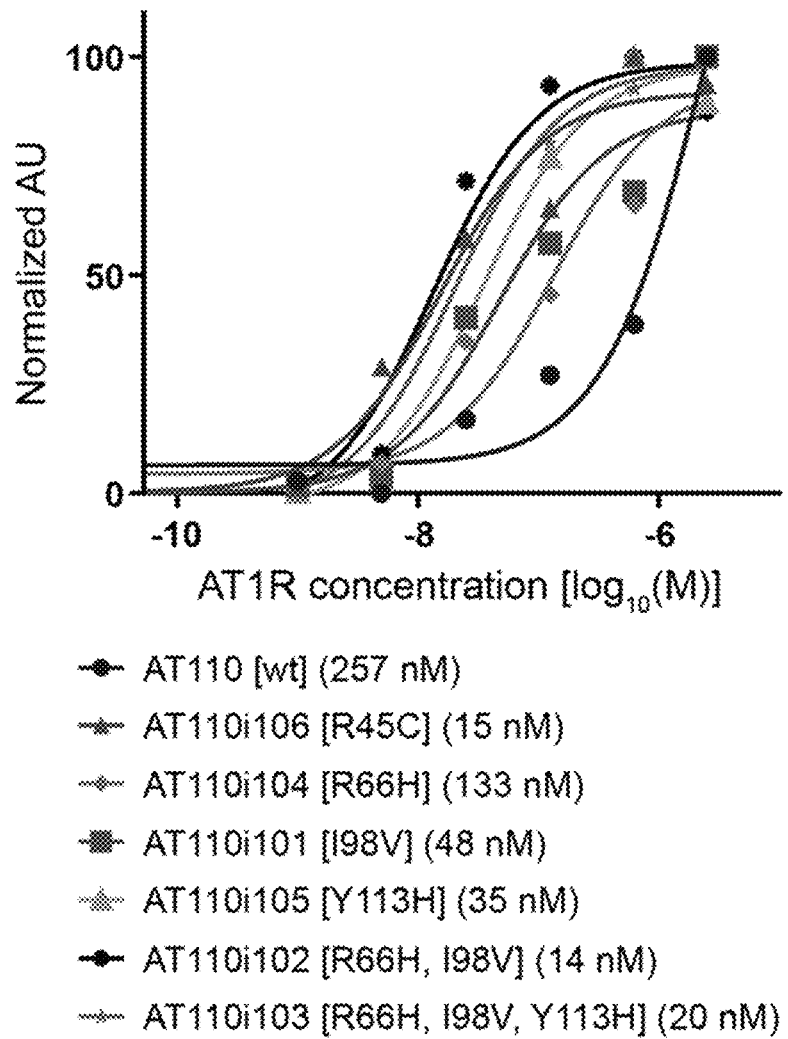
FIG. 7 summarizes the results of on-yeast binding assays of AT110 and AT110 mutants obtained by epOrthoRep, YSD, and sequence diversification as described herein.

In on-yeast affinity assays, each of the dominant mutations conferred higher affinity for AT1R compared to the parental sequence, AT110, as summarized in FIG. 7. The results of these assays indicate that epOrthoRep and YSD may be used to artificially evolve (i.e., mutate and select in vivo) proteins to have a desired characteristic.

The results of radioligand competition binding assays indicate that the amino acid mutations resulting from artificial evolution in vivo more effectively stabilize agonist binding in the present of antagonist, thereby indicating increased affinity, compared to the parental sequence, AT110. See FIG. 8. As shown in FIG. 8, the single mutation R66H minimally increases affinity and the single mutation Y113H causes a decrease in affinity compared to the parental sequence. However, these two mutations are found in combination with other mutations in the artificially evolved proteins which exhibit significantly increased affinities. Therefore, artificial evolution of mutant proteins as described herein considers interactions between mutations such that a mutation, which by itself does not confer the desired characteristic, may evolve in combination with another mutation to confer the desired characteristic. Such interactions may include epistatic interactions. These results also indicate that a protein based on the parental sequence may be engineered to have (or exclude) one or more of the amino acid mutations to further modify the desired characteristic, e.g., fine-tune (increase or decrease) the functional activity of the protein compared to the evolved mutants.

Therefore, the combination of epOrthoRep and YSD can be used to artificially evolve proteins in vivo to have a desired characteristic by successive rounds sequence diversification and selection of surface displayed proteins. The combination of epOrthoRep and YSD allow parallelized diversification and selection of proteins for one or more desired characteristics (e.g., affinity for one or more target ligands). Also, as described herein, the ability to use different stringency and biochemical conditions to select mutants to be subjected to further sequence diversification, confers the ability to selectively design or obtain proteins having a desired level of activity, e.g., a desired affinity or enzymatic activity. The combination of epOrthoRep and YSD may also be used to artificially and simultaneously evolve two or more proteins having different desired characteristics where the characteristics of one may impact the other by selecting for each of the desired characteristics of the two or more proteins.

YSD Optimization

Although the fractions of cells displayed levels of protein that was sufficient for selection and enrichment, the level of YSD was low (~1%). Therefore, further modifications were made to increase YSD of proteins obtained by epOrthoRep. Specifically, the wild-type pre-pro secretory leader sequence of the P1 plasmid of F102 was replaced with app8 (SEQ ID NO: 6), the p10B2 promoter was replaced with pGA (SEQ ID NO: 7), and a cloning protocol that avoids PCR amplification of the circular P1 integration plasmid was employed.

As shown in FIG. 9, the pGA promoter more than tripled YSD compared to the p10B2 promoter. The sequence for the pGA promoter differs from p10B2 by a G to A at the −5 position and a G to A at the −34 position. Interestingly, the mutations result in TATA sequences, which are known to recruit RNA polymerase and enhance transcription. Therefore, in some embodiments, the promoter of the P1 expression plasmid is a constitutively active promoter that has one or more TATA sequences.

The combination of these modifications resulted in a dramatic increase in YSD from undetected to 40% of cells displaying proteins from epOrthoRep of AT110 (data not shown). Specifically, after initial construction of the P1 expression plasmid that resulted in detectable YSD, all cells showed undetectable expression of proteins against AT1R. After modifying the secretory leader sequence, roughly 8% of cells weakly expressed protein, such that no antigen binding could be detected. After modifying the P1 expression plasmid to have a polyA tail and the pGA promoter, 40% of cells express protein, and antigen binding could be detected for about half of the 40%.

FIG. 10 is a sequence alignment showing the mutations resulting from artificial evolution of AT110 (parental sequence) using error-prone PCR methods in the prior art (AT10il) and epOrthoRep combined with YSD as disclosed herein (pGA Mutant). One may reasonably expect that artificial evolution of a given protein for the same desired characteristic using an error prone replication method in the art combined with a selection and enrichment strategy in the art would likely result in the same mutations obtained by using another artificial evolution method (i.e., a different error prone replication method combined with the same or different selection and enrichment strategy or vice versa). Unexpectedly, however, as evidenced by the sequence alignment of FIG. 10, the combination of epOrthoRep and YSD provides different combinations of mutations, that may result in mutants exhibiting superior activity levels of the desired characteristic.

Strain for epOrthoRep and YSD

A yeast host cell comprising the components required for both epOrthoRep and YSD was created as follows: The P1 plasmid in F102 was modified to have a selection marker that is not also used subsequently during epOrthoRep and YSD. The met15 gene was selected as the selection marker; however, any selection marker that is not subsequently used during epOrthoRep and YSD may be employed. The endogenous met15 genes in both F102 and EBY100 were knocked out by replacement with a linear PCR product encoding the KanMX gene flanked by sequences homologous upstream and downstream to the met15 ORF. Replacement of the endogenous met15 genes was confirmed using methods in the art. Then, the P1 plasmid of the F102 met15::KanMX was modified to contain the met15 gene to result in a P1 plasmid (referred to herein as "Landing Pad") encoding the wild-type TP-DNAP1 and met15. The sequence of the Landing Pad is:

(SEQ ID NO: 8)
ACACATAACATAGGGGAGAGTACTAAAAGTGAGATTATTGGAAGATTAGTACGTCTCCATTTTTT

TCTGTTTTTTTGTTTTTATATATTAGGTTATTTTTTTTCAGTTTTATATCAACTCTGTATAACAA

GTCTATTTTTTTATATTTTAAGTCTATTTTACACTTTTGACCTATAAGTCATTTTATTATACACA

TTTTCCAACTATAATATATGAATTACATTATTAATTTAAAAATGGATTACAAAGATAAGGCTTTA

AATGATCTAAGAAATGTATATGCCGACTTTGATTCACTTCCTTTAGATTTTAGACAAATATTAAT

AAAAGATAGAGCCACACTTCTTCAAAAAGAAGATGTAGAAAAGAAAATATTGGAAAGACAAGAAG

ATGCAAAGAAATATGCAGAATATTTAAAACAATCAGAAATACCAGAACGAATATCTTTGCCTAAC

ATTAAAAGACATAAAGGTGTTTCTATATCTTTTGAAGAAACATCAGAAGATATGGTTTTGGAACC

AAGACCTTTTATTTTTGATGGATTAAATATTAGATGTTTTAGACGAGAGACAATTTTCTCTCTCA

AAAATAAAATATTAAACATGGTAAAAGAAAGTTCTTCTTTTAAAAATGTTTCTAGACAATCAGTT

TCTTTCATGTATTTTAAAATTTTTAATAAAGGGAAAGTTATAGCTTCTACAAAAAGTGTAAATAT

TTATGAAGATAAAATAGATGAGAGATTAGAAGATTTGTGTAATAATTTTGACGATGTATTAAAGA

AAATTATAGATGTAACTTATGGTTATGAAAGTTTATTTGTTTCAGAAACATATTCTTATGTTATA

TTTTATGCTAAATCTATATATTTCCCTCAACCTAGATGTGTGAATAATTGGGGTAATAATATTCC

TAATATTCTTACTTTCGATAGTTTTAAGCTTTTCACAGCTAATAAAAATAATGTTTCTTGTATTA

AACAGTGCTCTCGTTTTCTGTGGCAAAAAGATTTTAATACATTAGAAGAAATGATAGAATATAAA

-continued

```
AATGGTAATATTTGTATAGTTACTCCTCAATTACATATAAATGATGTAAGAGACATAAAATCATT

TAACGACATACGTTTATATTCAGAAAGTCCTATTAAAACATTCAGTGTTATAGATAATACTATAA

CATATTTGTTTTATTTTAAAGAACATTTAGGAGTTATATTTAATATTACTAAATCCAGACATGAT

AGAAGAGTCACTAAATTTAGTCCTTTGTCAAAATTTTCTGATGTTAAAAATATAACAGTATGTTT

TGATATAGAATCTTATTTTGATCCAGAAAAAGAATCTAATCAAGTTAATATACCCTTTATATGTT

GTGCATCTATAATATATAATAAAGTCATAGGAAATATTGTAGATTTTGAAGGAAGAGATTGTGTA

GCTCAAATGATAGAATATGTTGTAGATATATGTGGAGAGCTTAATATATCTTCAGTGGAACTAAT

TGCACATAATGGTGGAGGTTATGATTTTCATTATATTTTAAGTAGTATGTATAATCCTGCAGCTA

TTAAAAATATATTAATTAGAAATAACTCATTTATAAGTTTTAATTTTGCTCACGATGGAGTCAAA

TTTTCTGTAAAAGATTCCTATAGTTTCTTGTTATGTAGTTTAGCAAATGCTTCAAAAGCATTTTT

AAACGAAGAAACCTTTAAGAAAACAGATTTTCCCCATCATGATTTAAAAACAGCAGATGATTTAT

ATAAAGTATATAAAGAATGGTCATCTGTAAACACTGAAATAAATCATGTAGTGGAAAAAGAAAAA

CTTCTTATAACATCAGAACATATAGTTAATTTCACTAAAAATGATAAATCTAAAACTCTAATAGA

ATGGTCTAAAGATTATTGTAGAAATGATGTTTTGGTTTTATCTAAGGTATGGTTAGAATTTAAAA

ATGCTGTAGAAGATATTTTTAATTGTGAATTAGTAGATCAAACTATGACATTAGCAGGACTAAGT

TATAAATTATTTCAAGCAAATATGCCTTTTGATGTTGAATTAAGACATCCAAATAAAGAAGATTA

TTTTAACATGAGAGAGGCTTTAATAGGAGGGAGATGTATTAGTGTCAATGGAATATATAAAGATG

TTTTATGTTTAGATGTAAAATCATTATATCCAGCATCTATGGCATTTTATGACCAGCCATATGGA

TCTTTCAAAAGAGTATCTAGTAGACCTAAAGATGAATTAGGTATTTATTATGTCAGAGTAACTCC

TAATAGAAATAATAAATCCAACTTTTTTCCTATAAGAAGTCACAATAAAATTACTTATAATAATT

TTGAAGAAAGTACATATATAGCATGGTATACAAATGTAGATATAGATATAGGTTTGTCTGAAGGT

CATAATATAGAATATATCCCCTTTGATTCTTATGGAAATATAGGTTATTCTTGGTCTAAAAAAGG

TAAAATATTCGAAAAATATATAAAAGACGTGCTGTACAAATTAAAAATAAAGTATGAAAAACAAA

ACAATAAAGTTAAAAGAAATGTTATCAAAATTATTATGAACAGTTTATGGGCAAATTCGCACAA

AAATGGGTAAATTTTGAGTATTTTATAAAATCAGAAGATGATATAGATTTTGAGTCAGAAGAGGC

ATATAAGATATGGGACACTGATTTTATGCTGATAAAGAAAATTAAAGAATCTACTTATTCATCTA

AACCTATACAAAATGGAGTATTTACATTAAGTTGGGCAAGATACCACATGAAAAGTATATGGGAT

GCAGGGGCTAAAGAAGGAGCAGAATGTATCTATTCGGACACAGATAGTATTTTTGTACATAAAGA

ACATTTTAAAAAGAATGCTAAATTTATGTTAAATGGTTTAAAAGTTCCTATTATAGGATCAGAAG

TAGGACAATTAGAATTAGAATGTGAGTTTGATAAATTGTTATGTGCAGGTAAAAAGCAATACATG

GGATTTTATACTTATTTTCAAGATGGAAAACCATGTATAAAAGAAAAGAAAAGATTTAAGGGTAT

TCCTAGTAATTATATAATACCTGAATTATATGCTCATTTACTTTCAGGTGCAGACAAAGAAGCTA

AAATACAATTTTTGAAATTTAGAAGAGAATGGGGATCAGTTAAAGGATATATAGAAAATAAGACC

GTGAAAGCTACTTAAGATCTTGTATAGATAAAAAATTACGTATATCATTTATAGATGGAGAAGTT

AATAAATTTTCTAAAAGAGGAAAATTAATTTCTAATGTGAACACTAGTGAGATAGCTAAAGATCT

TAATTGTGAAAACAATATTGAAAGTATAATAAATACATTAAAAGAACAAAATAGATATTTTGACA

AACAAATTGCATATGCCATCTCATTTCGATACTGTTCAACTACACGCCGGCCAAGAGAACCCTGG

TGACAATGCTCACAGATCCAGAGCTGTACCAATTTACGCCACCACTTCTTATGTTTTCGAAAACT

CTAAGCATGGTTCGCAATTGTTTGGTCTAGAAGTTCCAGGTTACGTCTATTCCCGTTTCCAAAAC

CCAACCAGTAATGTTTTGGAAGAAAGAATTGCTGCTTTAGAAGGTGGTGCTGCTGCTTTGGCTGT

TTCCTCCGGTCAAGCCGCTCAAACCCTTGCCATCCAAGGTTTGGCACACACTGGTGACAACATCG
```

-continued

```
TTTCCACTTCTTACTTATACGGTGGTACTTATAACCAGTTCAAAATCTCGTTCAAAAGATTTGGT

ATCGAGGCTAGATTTGTTGAAGGTGACAATCCAGAAGAATTCGAAAAGGTCTTTGATGAAAGAAC

CAAGGCTGTTTATTTGGAAACCATTGGTAATCCAAAGTACAATGTTCCGGATTTTGAAAAAATTG

TTGCAATTGCTCACAAACACGGTATTCCAGTTGTCGTTGACAACACATTTGGTGCCGGTGGTTAC

TTCTGTCAGCCAATTAAATACGGTGCTGATATTGTAACACATTCTGCTACCAAATGGATTGGTGG

TCATGGTACTACTATCGGTGGTATTATTGTTGACTCTGGTAAGTTCCCATGGAAGGACTACCCAG

AAAAGTTCCCTCAATTCTCTCAACCTGCCGAAGGATATCACGGTACTATCTACAATGAAGCCTAC

GGTAACTTGGCATACATCGTTCATGTTAGAACTGAACTATTAAGAGATTTGGGTCCATTGATGAA

CCCATTTGCCTCTTTCTTGCTACTACAAGGTGTTGAAACATTATCTTTGAGAGCTGAAAGACACG

GTGAAAATGCATTGAAGTTAGCCAAATGGTTAGAACAATCCCCATACGTATCTTGGGTTTCATAC

CCTGGTTTAGCATCTCATTCTCATCATGAAAATGCTAAGAAGTATCTATCTAACGGTTTCGGTGG

TGTCTTATCTTTCGGTGTAAAAGACTTACCAAATGCCGACAAGGAAACTGACCCATTCAAACTTT

CTGGTGCTCAAGTTGTTGACAATTTAAAGCTTGCCTCTAACTTGGCCAATGTTGGTGATGCCAAG

ACCTTAGTCATTGCTCCATACTTCACTACCCACAAACAATTAAATGACAAAGAAAAGTTGGCATC

TGGTGTTACCAAGGACTTAATTCGTGTCTCTGTTGGTATCGAATTTATTGATGACATTATTGCAG

ACTTCCAGCAATCTTTTGAAACTGTTTTCGCTGGCCAAAAACCATGAAAAACTGTATTATAAGTA

AATGCAGGTATACTAAACTCACAAATTAGAGCTTCAATTTAATTATATCAGTTATTACCCGAGCT

CCGTTTCTATTATGAATTTCATTTATAAAGTTTATGTACAAATATCATAAAAAAAGAGAATCTTT

GGATCCAGAGATATAAAATTTAATATGGAAAAAATAAGACAAGAAAGATACAACCAAATGAAAGA

AGCTCTAAATAGTGTTGAAGGTTATAAAGGAAAAATTGTAGCCTCAGACTCAGATTGGTGTTTCA

AAGATCCTCAAGGCAATAGAATAACAGATTTTGATAGTATTAATAAAGAATTAGGTCTTGGTAGA

AGAGATGTAAAATTAGATAAAGGTCATGATGATTTAATTAAATTATGTACTGAAAAAATAGATAG

TATGAATAATCTACAGAATGGAAAATGTGTATAATAAAATGACTTATAGGTCAAAAGTGTAAAAT

AGACTTAAAATATAAAAAAATAGACTTGTTATACAGAGTTGATATAAAACTGAAAAAAAATAACC

TAATATATAAAAACAAAAAAACAGAAAAAAATGGAGACGTACTAATCTTCCAATAATCTCACTTT

TAGTACTCTCCCCTATGTTATGTGT
```

Figure 11:
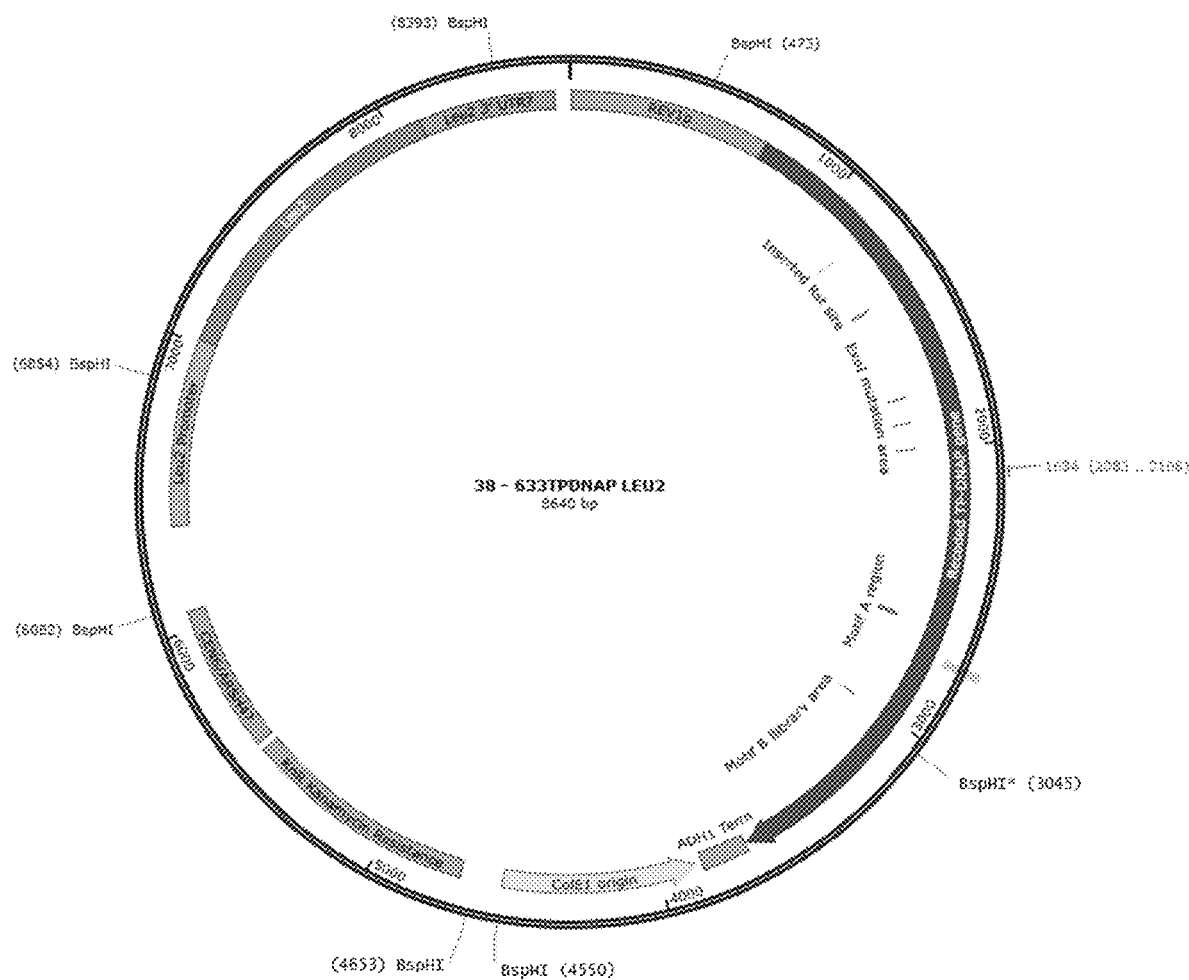

A yeast cell comprising the Landing Pad was fused with an EBY100 met15::KanMX yeast cell using protoplast fusion methods in the art. The yeast cell was propagated on synthetic complete media lacking histidine and uracil (to select for EBY100 genomic markers), and lacking methionine and cysteine (to select for the Landing Pad). The resulting yeast cell strain contained the nucleus EBY100 met15::KanMX and the Landing Pad in the cytoplasm. The strain was then transformed with the CEN/ARS plasmid schematically shown in FIG. 11 to provide expression of an error prone TP-DNAP1. Although the CEN/ARS plasmid expresses the error prone TP-DNAP1 (AKA 633) and has a Leu2 selection marker, any plasmid that expresses an error prone TP-DNAP1 and suitable selection maker may be used. The final yeast strain comprises the nucleus EBY100 met15::KanMX, the Landing Pad, the CEN/ARS plasmid, and the requisite components for orthogonal replication and transcription of a P1 expression plasmid.

Specialized Integration Plasmids

Figure 12:
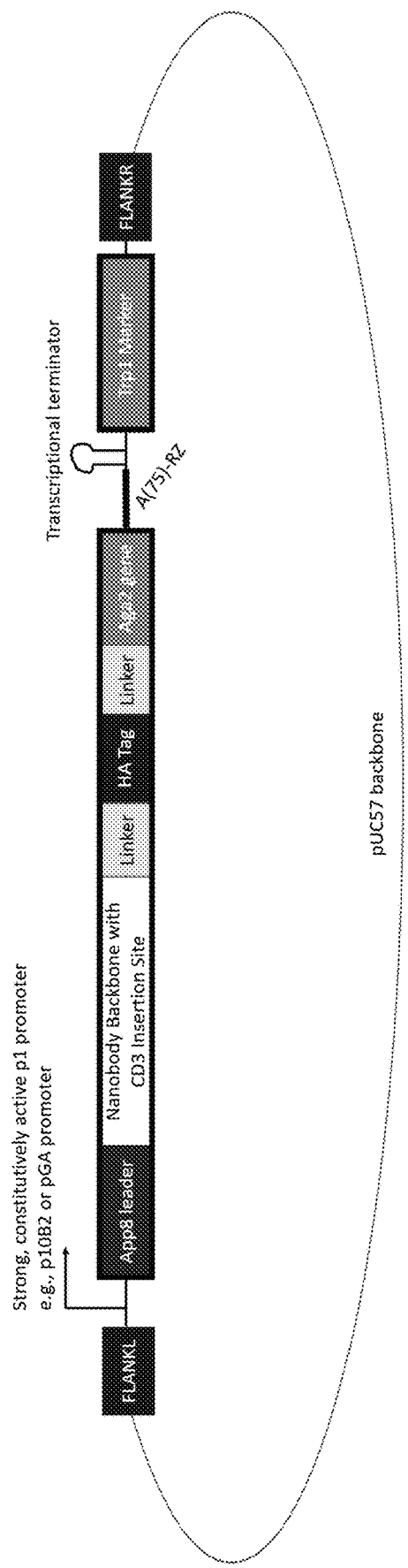

Instead of recombinantly inserting an entire nanobody sequence into a P1 expression plasmid, a specialized P1 integration plasmid was created for YSD of nanobodies. The P1 integration plasmid contains a nanobody scaffold sequence downstream of the app8 sequence, followed by a flexible linker containing an HA tag (SEQ ID NO: 9), the AGA2 gene, polyA(75) tail, and a Hammerhead self-cleaving ribozyme such as (SEQ ID NO: 3). The nanobody scaffold sequence contains a CDR3 insert region where a CDR3 sequence of interest may be easily inserted using recombinant techniques. The specialized CDR3 P1 integration plasmid is schematically shown in FIG. 12.

The following is an exemplary nanobody scaffold sequence where the X's exemplify the CDR3 insert region:

(SEQ ID NO: 10)
EVQLVESGGGLVQAGGSLRLSCAASGFTFSSYAMGWYRQAPGKEREFVA

AISWSGGSTYYADSVKGRFTISRDNAKNTVYLQMNSLKPEDTAVYYCXX

XXXXXXXGQGTQVTVSS

This specialized CDR3 P1 integration plasmid allows a plurality of P1 integration plasmids to be constructed from a plurality of CDR3 sequences, such as those obtained from a library of CDR3 sequences. The plurality of P1 integration plasmids allows the artificial evolution of a plurality of nanobodies (compared to the artificial evolution of a single nanobody) using epOrthoRep and YSD as described herein.

Other specialized P1 integration plasmids may be similarly made for the artificial evolution of CDR1 and CDR2 sequence and other proteins. For example, the nanobody backbone sequence may be replaced with a backbone sequence of a given protein that presents an active site of, e.g., an enzyme. The position of the active site in the backbone sequence is the target location where a parental sequence is inserted. Then a library of active sites are artificially evolved to have greater enzymatic activity against a given substrate.

Alternatively, the Landing Pad as described herein may be modified such that it contains the secretory leader sequence (e.g., app8), HA tag, attachment sequence (e.g., AGA2), polyA tail and ribozyme, transcriptional terminator, and selection marker such that the parental sequence need only be inserted by homologous recombination.

The methods, compositions, and kits described herein may be used to design an affinity reagent having one or more desired characteristics.

Optimized epOrthoRep

The app8 secretory leader sequence was modified to encode a V10A mutation, which is herein referred to as app8il. The app8 and app8il amino acid sequences are as follows:

```
app8:
                                    (SEQ ID NO: 6)
MRFPSIFTAVLFAASSALAAPVNTTTEDETAQIPAEAVIDYSDLEGDFDA

AALPLSNSTNNGLSSTNTTIASIAAKEEGVQLDKR app8il:
                                    (SEQ ID NO: 11)
MRFPSIFTAALFAASSALAAPVNTTTEDETAQIPAEAVIDYSDLEGDFDA

AALPLSNSTNNGLSSTNTTIASIAAKEEGVQLDKR
```

The app8il secretory leader sequence resulted in about a 90% improvement in expression over the app8 secretory leader sequence. Thus, in some embodiments, the secretory leader sequence is app8il. Additionally, the combination of the app8il secretory leader sequence with the antigen binding protein expressed as an N-terminus fusion, i.e., fused to at its N-terminus, resulted in about a 25-fold improvement in protein display over methods using the wild-type pre-pro secretory leader sequence (MFα1pp), p10B2, with the antigen binding protein fused at its C-terminus, and without a polyA tail with a self-cleaving ribozyme sequence. That is, optimizing the epOrthoRep method described herein by using app8il instead of app8, pGA instead of p10B2, and expressing the antigen binding protein as an N-terminal fusion resulted in a 25-fold improvement in protein display over prior art methods (i.e., yeast display systems employing p10B2+MFα1pp+C-terminus fusion without the polyA tail and self-cleaving ribozyme sequence). Therefore, in some embodiments, the secretory leader sequence is app8il, the constitutively active P1 promoter is pGA, and the antigen binding sequence is provided as an N-terminus fusion.

Figure 13:
Figure 14:
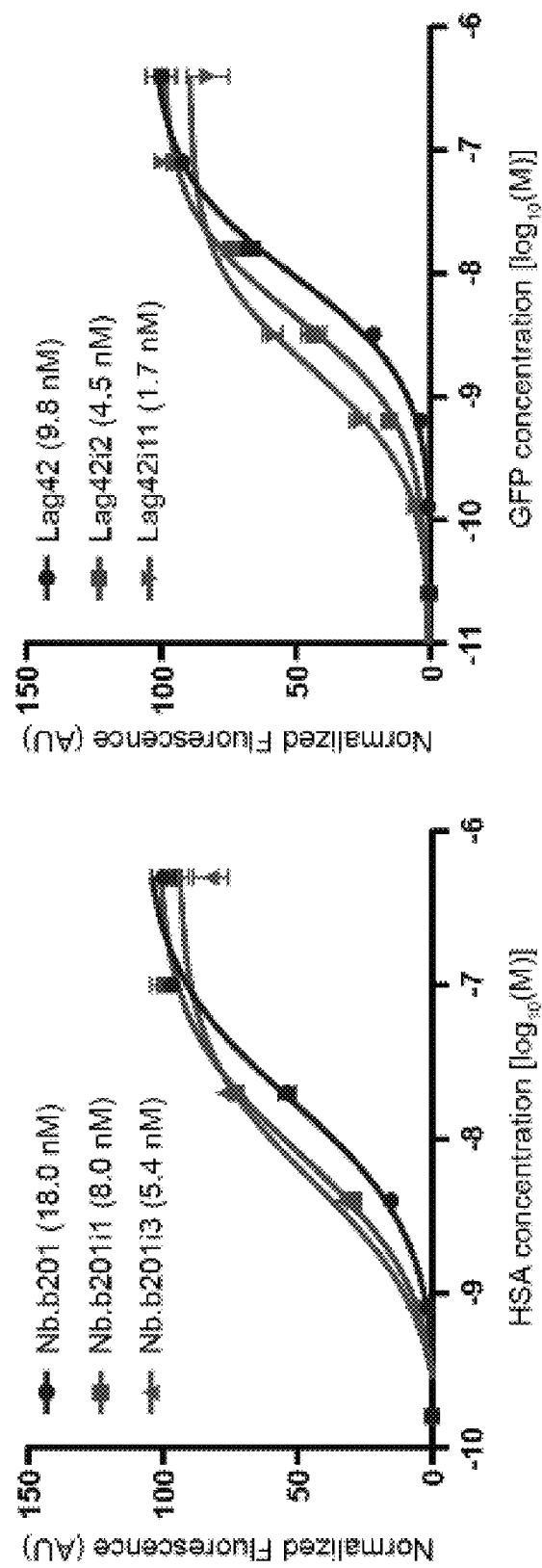

To validate the optimized epOrthoRep method, 4-6 cycles of epOrthoRep were run as above using P1 integration plasmids containing the pGA promoter and the app8il leader sequence as schematically represented in FIG. 13 and nanobody Nb.b201, which binds human serum albumin (HSA), and nanobody Lag42, which binds green fluorescent protein (GFP) as the parental nanobodies encoded thereon. FIG. 14 shows the affinities of the evolved nanobodies for their target antigen.

Evolution of SARS-COV-2 Nanobodies

Starting from an open-source naïve nanobody YSD library, 8 nanobodies that bind the receptor-binding domain (RBD) of the SARS-CoV-2 spike (S) protein were selected for use as parental sequences. Each nanobody was independently encoded on the P1 integration plasmid schematically shown in FIG. 13 at the indicated "nanobody" region. Using the "optimized epOrthoRep method" above, 3-8 cycles of epOrthoRep were performed (which essentially took no more than 3 days). Optimized epOrthoRep resulted in mutants that exhibit higher affinities for RBD than the given parental nanobody. Notably, mutants RBD1i13, RBD3i17, RBD6id, RBD10i10, RBD10i14, and RBD11i12 exhibited monovalent RBD-binding affinity improvements of up to about 580-fold over the course of affinity maturation, and one nanobody, RBD10i14, reached a subnanomolar monovalent $K_d$ of 0.72 nM.

Anti-RBD Nanobodies Neutralize SARS-CoV-2 Pseudovirus

The mutant nanobodies exhibit exceptional neutralization potencies that are upto about a 925-fold improvement over the given parental nanobody. For example, nanobodies RBD1i13, RBD3i17, RBD6id, RBD10i10, RBD10i14, and RBD11i2 exhibited low nanomolar or subnanomolar half-maximal inhibitory concentration ($IC_{50}$) values of 0.66, 1.51, 0.72, 2.44, 5.38, and 0.52 nM, respectively. The activities of the parental nanobodies and the evolved mutants are shown in FIG. 15.

Interestingly, nanobodies RBD1i13 and RBD11i12, which had the strongest viral neutralization potencies among all evolved variants, were evolved from parental nanobodies that were relatively poor neutralizers.

Anti-RBD Nanobodies Exhibit Diversity in Inhibition Modes

To understand how evolved anti-RBD nanobodies inhibit SARS-CoV-2 pseudovirus infection, potent neutralizers were tested for their ability to compete with ACE2 in binding to RBD. Nanobodies RBD1i13, RBD6id, and RBD11i12 strongly or moderately competed with ACE2 whereas a fourth clone, RBD10i10, did not. This suggests that different nanobodies bind RBD at different locations, which may translate to potency against diverse SARS-CoV-2 variants.

These results were analyzed using methods in the art to reveal single mutations in RBD that escape nanobody binding. In this assay, a library of yeast-displayed RBD mutants representing every single amino acid change was first sorted for those that maintain binding to soluble human ACE2, then labeled with each nanobody under investigation, and finally sorted for low nanobody labeling. This result is the enrichment of functional RBD mutants that escape nanobody binding.

This mutational scanning assay elucidated different degrees of ACE2 competition by nanobodies RBD1i13, RBD10i10 and RBD11i12 were observed. Specifically, RBD mutations that escape binding by RBD1i13's parent nanobody, RBD1i1, are immediately adjacent to the ACE2 binding site when mapped to the structure of the RBD/ACE2 complex, while the RBD mutations that escape nanobody RBD10i10 are not. RBD mutations that escape nanobody RBD11i12 are physically closer to ACE2 than those that escape nanobody RBD10i10 but more distal to ACE2 than those that escape nanobody RBD1i13, consistent with the observation that RBD11i12 competes with ACE2 binding to RBD more modestly than RBD1i13. Notably, mutations in RBD capable of escaping nanobodies RBD1i13 and RBD10i10 do not include the concerning E484K and N501Y RBD mutations of various SARS-CoV-2 variants, although all three nanobodies have reduced binding to SARS-CoV-2 variants having an L452 RBD mutation.

A Naïve Nanobody Library can be Encoded on Ahead

In the experiments described above, parental nanobodies were individually encoded on a P1 integration plasmid.

In alternative embodiments, a library of proteins of interest may be computationally designed and then each protein is then encoded on P1 integration plasmids to form a library of yeast strains, each containing one of the P1 integration plasmids encoding one of the proteins of interest. Then the library of yeast strains may be concurrently subjected to rounds of epOrthoRep against a given target of interest.

Figure 16:
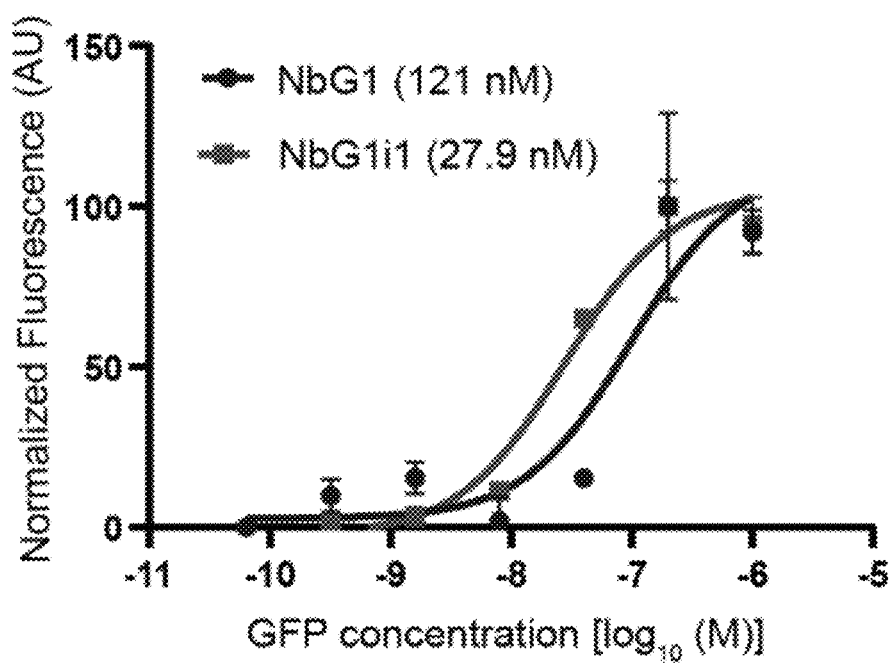

To test the feasibility of this approach, a 200,000-member naïve nanobody library capturing key features of camelid immune repertoires was computationally designed and synthesized and encoded on P1 integration plasmids. The P1 integration plasmids were then used to create a library of yeast strains with 50-fold coverage, which were then subjected to selection for binding GFP as the target of interest. After three rounds, a single nanobody, NbG1, dominated the population, and after two additional cycles, a C96Y mutation that increased GFP binding ($EC_{50}$) by 4.4-fold arose and fixed as NbG1i1. See FIG. 16.

This shows that epOrthoRep as disclosed herein emulates the process of somatic recombination, clonal expansion, and somatic hypermutation in the immune system. Therefore, the methods herein may be used to design nanobodies de novo-computationally design nanobodies and use epOrthoRep to evolve them into nanobodies that bind a desired target.

The sequences of the nanobodies disclosed herein are set forth in Table 2 as follows:

TABLE 2

| Name | Sequence (Bold = mutation from corresponding parent; only non-synonymous mutations are indicated) | SEQ ID NO: | Target |
|---|---|---|---|
| AT110 | QVQLQESGGGLVQAGGSLRLSCAASGNIFDADIMGWYRQAPGKERELVASITDGGSTNYADSVKGRFTISRDNAKNTVYLQMNSLKPEDTAVYYCAAIAYPDIPTYFDYDSDYFYWGQGTQVTVSSS | 4 | AT1R |
| AT110i101 | QVQLQESGGGLVQAGGSLRLSCAASGNIFDADIMGWYRQAPGKERELVASITDGGSTNYADSVKGRFTISRDNAKNTVYLQMNSLKPEDTAVYYCAAVAYPDIPTYFDYDSDYFYWGQGTQVTVSSS | 12 | AT1R |
| AT110i102 | QVQLQESGGGLVQAGGSLRLSCAASGNIFDADIMGWYRQAPGKERELVASITDGGSTNYADSVKGHFTISRDNAKNTVYLQMNSLKPEDTAVYYCAAVAYPDIPTYFDYDSDYFYWGQGTQVTVSSS | 13 | AT1R |
| AT110i103 | QVQLQESGGGLVQAGGSLRLSCAASGNIFDADIMGWYRQAPGKERELVASITDGGSTNYADSVKGHFTISRDNAKNTVYLQMNSLKPEDTAVYYCAAVAYPDIPTYFDYDSDHFYWGQGTQVTVSSS | 14 | AT1R |
| AT110i104 | QVQLQESGGGLVQAGGSLRLSCAASGNIFDADIMGWYRQAPGKERELVASITDGGSTNYADSVKGHFTISRDNAKNTVYLQMNSLKPEDTAVYYCAAIAYPDIPTYFDYDSDYFYWGQGTQVTVSSS | 15 | AT1R |
| AT110i105 | QVQLQESGGGLVQAGGSLRLSCAASGNIFDADIMGWYRQAPGKERELVASITDGGSTNYADSVKGRFTISRDNAKNTVYLQMNSLKPEDTAVYYCAAIAYPDIPTYFDYDSDYHWGQGTQVTVSSS | 16 | AT1R |
| Nb.b201 | QVQLQESGGGLVQAGGSLRLSCAASGYISDAYYMGWYRQAPGKEREFVATITHGTNTYYADSVKGRFTISRDNAKNTVYLQMYSLKPEDTAVYYCAVLETRSYSFRYWGQGTQVTVSS | 17 | HSA |
| Nb.b201i1 | QVQLQESGGGLVQAGGSLRLSCAASGYISDAYYMGWYRQAPGKERGFVATITHGTNTYYADSVKGRFTISRDNAKNTVYLQMNSLKPEDTAVYYCAVLETRSYSFRYWGQGTQVTVSS | 18 | HSA |
| Nb.b201i3 | QVQLQESGGGLVQAGGSLRLSCAASGYISDAYYMGWYRQAPGKEREFVATITHGTNTYYADSVKGRFTISRDNAKNTVYLQMNSLKPEDTAVYYCAVLETRSYSFRYWGQGTQVTVSS | 19 | HSA |
| Lag42 | MADVQLVESGGGLVQAGDSLRLSCAASGPTGAMAWFHQGLGKEREFVGGISPSGDNIYYADSVKGRFTIDRDNAKNTVSLQMNSLKPEDMGVYYCAARRRVTLFTSRTDYEFWGRGTQVTVS | 20 | GFP |
| Lag42i2 | MADVQLVESGGGLVQAGDSLRLSCAASGPTGAMAWFHQGLGKEREFVGGISPSGDDIYYADSVKGRFTIDRDNAKNTVSLQMNSLKPEDMGVYYCAARRRVTLFTSRTDYEFWGRGTQVTVS | 21 | GFP |
| Lag42i11 | MADVQLVESGGGLVQAGDSLRLSCAASGPTGAMAWFHQGLGKEREFVGGISPSGDDIYYADSVKGRFTIDRDNAKNTVSLQMNSLKPEDMGVYYCAARRRVTLFTSRTDYGFWGRGTQVTVS | 22 | GFP |

TABLE 2-continued

| Name | Sequence (Bold = mutation from corresponding parent; only non-synonymous mutations are indicated) | SEQ ID NO: | Target |
|---|---|---|---|
| RBD1 | QVQLQESGGGLVQAGGSLRLSCAASGTISYENFMGWYRQAPGKERELVAGINDGTNTYYADSVKGRFTISRDNAKNTVYLQMNSLKPEDTAVYYCAVIGTSVLGHAYWGQGTQVTVSS | 23 | RBD |
| RBD1i1 | QVQLQESGGGLVQAGGSLRLSCAASGTISYENFMGWYRQAPGKERKLVAGINDGTNTYYADSVKGRFTISRDNAKNTVYLQMNSLKPEDTAVYYCAVIGASVLGHAYWGQGTQVTVSS | 24 | RBD |
| RBD1i13 | QVQLQESGGGLVQAGGSLRLSCAASGTISYENFMGWYRQAPGKGRKLVAGINDGTNTYYADSVKGRFTISRDNAKNTVYLQMNSLEPEDTAVYYCAVIGASVLGHAYWGQGTQVTVSS | 25 | RBD |
| RBD3 | QVQLQESGGGLVQAGGSLRLSCAASGNISDFRFMGWYRQAPGKERELVAAIGRGSNTYYADSVKGRFTISRDNAKNTVYLQMNSLKPEDTAVYYCAARNATYPYYVYWGQGTQVTVSS | 26 | RBD |
| RBD3i2 | QAQLQESGGGLVQAGGSLRLSCAASGNISDFRFMGWYRQAPGKERELVAAIGRGSNTRYADSVKGRFTISRDNAKNTVYLQMNSLKPEDTAVYYCAARNATYPYYVYWGQGTQVTVSS | 27 | RBD |
| RBD3i17 | QAQLQESGGGLVQAGGSLRLSCAASGNISDFRFMGWYRQAPGKERELVAAIGRGSNTRCADSVKGRFTISRDNAKNTVYLQMNSLKPEDTAVYYCAARNATYPYYVYWGQGTQVTVSS | 28 | RBD |
| RBD6 | QVQLQESGGGLVQAGGSLRLSCAASGSISTTYLMGWYRQAPGKEREFVATINRGGSTYYADSVKGRFTISRDNAKNTVYLQMNSLKPEDTAVYYCAVGWPDPDYGLAYHRYWGQGTQVTVSS | 29 | RBD |
| RBD6id | QVQLQESGGGLVQAGGSLRLNCAANGSISTTYLMGWYRQAPGKEREFVATINRGGSTYYAISVKGRFTISRDNAKNTVYLQMNSLKPEDTAVYYCAVGWPDPDYGLAYHRYWGQGTQVTVSS | 30 | RBD |
| RBD6i10 | QVQLQESGGGLVQAGGSLRLNCAASGSISTTYLMGWYRQAPGKERKFVATINRGGSTYYAVSVKGRFTISRDNAKNTVYLQMNSLKPEDTAVYYCAVGWPDPDYGLAYHRYWGQGTQVTVNS | 31 | RBD |
| RBD6i13 | QVQLQESGGGLVQAGGSLRLNCAASGSISTTYLMGWYRQAPGKERKFVATINRGGSTYYAVSVKGRFTISRDNAKNTVYLQMNSLKPEDTAVYYCAVGWPDPGYGLAYHRYWGQGTQVTVNS | 32 | RBD |
| RBD7 | QVQLQESGGGLVQAGGSLRLSCAASGYISGAYYMGWYRQAPGKEREFVAGIGGGSTNYADSVKGRFTISRDNAKNTVYLQMNSLKPEDTAVYYCAVYQSVAYYYRGYFSYWGQGTQVTVSS | 33 | RBD |
| RBD7i12 | QVQLQESGGGLVQAGGSLRLSCAASGYISGAYYMGWYRQAPGKEREFVAGIGGGSTNYADSVKGRFTISRDNAKNTVYLQMNSLKPEDTAVYYCAVYQSVAYYCRGYFSYWGQGTQVTVSS | 34 | RBD |
| RBD7i13 | QVQLQESGGGLVQAGGSLRLSCAASGYISGAYYMGWYRQAPGKERKFVAGIGGGSTNYADSVKGRFTISRDNAKNTVYLQMNSLKPEDTAVYYCAVYQSVAYYCRGYFSYWGQGTQVTVSS | 35 | RBD |
| RBD8 | QVQLQESGGGLVQAGGSLRLSCAASGTIFGGPWMGWYRQAPGKEREFVAAIARGGNTNYADSVKGRFTISRDNAKNTVYLQMNSLKPEDTAVYYCAARDAVYPYLKYWGQGTQVTVSS | 36 | RBD |
| RBD8i1 | QVQLQESGGGLVQAGGSLRLSCAASGTISGGPWMGWYRQAPGKEREFVAAIARGGNTNYADSVKGRFTISRDNAKNTVYLQMNSLKPEDTAVYYCAARDAVYPYLKYWGQGTQVTVSS | 37 | RBD |
| RBD9 | QVQLQESGGGLVQAGGSLRLSCAASGYIFYSRRMGWYRQAPGKEREFVATIGHGTSTYYADSVKGRFTISRDNAKNTVYLQMNSLKPEDTAVYYCAALPRPHGAGTADARYNLWYWGQGTQVTVSS | 38 | RBD |
| RBD9i10 | QVQLQESGGGLVQAGGSLRLSCAASGYIFYSRRMGWYRQAPGKEREFVATIGHGASTYYAGSVKGRFTISRDNAKNTVYLQMDSLKPEDTAVYYCAALPRPHGAGTADARYNLWYWGQGTQVTVSS | 39 | RBD |
| RBD10 | QVQLQESGGGLVQAGGSLRLSCAASGTIFQVGSMGWYRQAPGKEREFVATIADGSSTNYADSVKGRFTISRDNAKNTVYLQMNSLKPEDTAVYYCAALGQVSEYNSASYEWTYPYWGQGTQVTVSS | 40 | RBD |

TABLE 2-continued

| Name | Sequence (Bold = mutation from corresponding parent; only non-synonymous mutations are indicated) | SEQ ID NO: | Target |
|---|---|---|---|
| RBD10i10 | QVQLQESGGGLVQAGGSLRLSCAASGTIFQVGSMGWYRQAPGKGRKFVATIADGGSTNYAGSVKGRFTISRDNAKNTVYLQMNSLKPEDTAVYYCAALGQVSEYNSASYEWTYPYWGQGTQVTVSS | 41 | RBD |
| RBD10i14 | QVQLQESGGGLVQAGGSLRLSCAASGTIFQVGSVGWYRQAPGKGRKFVATIADGSSTNYAGSVKGRFTISRDNAKNTVYLQMNSLKPEDTAVYYCAALGQVSEYNSASYEWTYPYWGQGTQVTVSS | 42 | RBD |
| RBD11 | QVQLQESGGGLVQAGGSLRLSCAASGNIFAKVWMGWYRQAPGKEREFVASIANGATTYYADSVKGRFTISRDNAKNTVYLQMNSLKPEDTAVYYCAARNWSGLGHFYWGQGTQVTVSS | 43 | RBD |
| RBD11i12 | QVQLQESGGGLVQAGGSLRLSCAASGNIFAKVWMGWYRQAPGKEREFVASIANGATTYYADSVKGRFTISRDNAKNTVYLQMNSLKPEDTAVYYCAARNWSGLGYFYWSQGTQVTVSS | 44 | RBD |
| RBD1-Fc | QVQLQESGGGLVQAGGSLRLSCAASGTISYENFMGWYRQAPGKERELVAGINDGTNTYYADSVKGRFTISRDNAKNTVYLQMNSLKPEDTAVYYCAVIGTSVLGHAYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 45 | RBD |
| RBD1i1-Fc | QVQLQESGGGLVQAGGSLRLSCAASGTISYENFMGWYRQAPGKERKLVAGINDGTNTYYADSVKGRFTISRDNAKNTVYLQMNSLKPEDTAVYYCAVIGASVLGHAYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 46 | RBD |
| RBD1i13-Fc | QVQLQESGGGLVQAGGSLRLSCAASGTISYENFMGWYRQAPGKGRKLVAGINDGTNTYYADSVKGRFTISRDNAKNTVYLQMNSLEPEDTAVYYCAVIGASVLGHAYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 47 | RBD |
| RBD3-Fc | QVQLQESGGGLVQAGGSLRLSCAASGNISDFRFMGWYRQAPGKERELVAAIGRGSNTYYADSVKGRFTISRDNAKNTVYLQMNSLKPEDTAVYYCAARNATYPYYVYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 48 | RBD |
| RBD3i2-Fc | QAQLQESGGGLVQAGGSLRLSCAASGNISDFRFMGWYRQAPGKERELVAAIGRGSNTRYADSVKGRFTISRDNAKNTVYLQMNSLKPEDTAVYYCAARNATYPYYVYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 49 | RBD |
| RBD3i17-Fc | QAQLQESGGGLVQAGGSLRLSCAASGNISDFRFMGWYRQAPGKERELVAAIGRGSNTRCADSVKGRFTISRDNAKNTVYLQMNSLKPEDTAVYYCAARNATYPYYVYWGQGTQVTVSSDKTHTCPPCPAPELLGGPSVFLFPPKPKDTLMISRTPEVTCVVVDVSHEDPEVKFNWYVDGVEVHNAKTKPREEQYNSTYRVVSVLT | 50 | RBD |

TABLE 2-continued

| Name | Sequence (Bold = mutation from corresponding parent; only non-synonymous mutations are indicated) | SEQ ID NO: | Target |
|---|---|---|---|
| | VLHQDWLNGKEYKCKVSNKALPAPIEKTISKAKGQPREPQV YTLPPSREEMTKNQVSLTCLVKGFYPSDIAVEWESNGQPEN NYKTTPPVLDSDGSFFLYSKLTVDKSRWQQGNVFSCSVMHE ALHNHYTQKSLSLSPGK | | |
| RBD6-Fc | QVQLQESGGGLVQAGGSLRLSCAASGSISTTYLMGWYRQAP GKEREFVATINRGGSTYYADSVKGRFTISRDNAKNTVYLQM NSLKPEDTAVYYCAVGWPDPDYGLAYHRYWGQGTQVTVSSD KTHTCPPCPAPELLGGPSVFLFPPKPKDTLMISRTPEVTCV VVDVSHEDPEVKFNWYVDGVEVHNAKTKPREEQYNSTYRVV SVLTVLHQDWLNGKEYKCKVSNKALPAPIEKTISKAKGQPR EPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGK | 51 | RBD |
| RBD6id-Fc | QVQLQE5GGGLVQAGGSLRLNCAANGSISTTYLMGWYRQAP GKEREFVATINRGGSTYYAISVKGRFTISRDNAKNTVYLQM NSLKPEDTAVYYCAVGWPDPDYGLAYHRYWGQGTQVTVSSD KTHTCPPCPAPELLGGPSVFLFPPKPKDTLMISRTPEVTCV VVDVSHEDPEVKFNWYVDGVEVHNAKTKPREEQYNSTYRVV SVLTVLHQDWLNGKEYKCKVSNKALPAPIEKTISKAKGQPR EPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGK | 52 | RBD |
| RBD6i10-Fc | QVQLQESGGGLVQAGGSLRLNCAASGSISTTYLMGWYRQAP GKERKFVATINRGGSTYYAVSVKGRFTISRDNAKNTVYLQM NSLKPEDTAVYYCAVGWPDPDYGLAYHRYWGQGTQVTVNSD KTHTCPPCPAPELLGGPSVFLFPPKPKDTLMISRTPEVTCV VVDVSHEDPEVKFNWYVDGVEVHNAKTKPREEQYNSTYRVV SVLTVLHQDWLNGKEYKCKVSNKALPAPIEKTISKAKGQPR EPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGK | 53 | RBD |
| RBD6i13-Fc | QVQLQESGGGLVQAGGSLRLNCAASGSISTTYLMGWYRQAP GKERKFVATINRGGSTYYAVSVKGRFTISRDNAKNTVYLQM NSLKPEDTAVYYCAVGWPDPGYGLAYHRYWGQGTQVTVNSD KTHTCPPCPAPELLGGPSVFLFPPKPKDTLMISRTPEVTCV VVDVSHEDPEVKFNWYVDGVEVHNAKTKPREEQYNSTYRVV SVLTVLHQDWLNGKEYKCKVSNKALPAPIEKTISKAKGQPR EPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGK | 54 | RBD |
| RBD7-Fc | QVQLQESGGGLVQAGGSLRLSCAASGYISGAYYMGWYRQAP GKEREFVAGIGGGSTNYADSVKGRFTISRDNAKNTVYLQMN SLKPEDTAVYYCAVYQSVAYYYRGYFSYWGQGTQVTVSSDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK | 55 | RBD |
| RBD7i12-Fc | QVQLQESGGGLVQAGGSLRLSCAASGYISGAYYMGWYRQAP GKEREFVAGIGGGSTNYADSVKGRFTISRDNAKNTVYLQMN SLKPEDTAVYYCAVYQSVAYYCRGYFSYWGQGTQVTVSSDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK | 56 | RBD |
| RBD7i13-Fc | QVQLQESGGGLVQAGGSLRLSCAASGYISGAYYMGWYRQAP GKERKFVAGIGGGSTNYADSVKGRFTISRDNAKNTVYLQMN SLKPEDTAVYYCAVYQSVAYYCRGYFSYWGQGTQVTVSSDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK | 57 | RBD |

TABLE 2-continued

| Name | Sequence (Bold = mutation from corresponding parent; only non-synonymous mutations are indicated) | SEQ ID NO: | Target |
|---|---|---|---|
| RBD10-Fc | QVQLQESGGGLVQAGGSLRLSCAASGTIFQVGSMGWYRQAP GKEREFVATIADGSSTNYADSVKGRFTISRDNAKNTVYLQM NSLKPEDTAVYYCAALGQVSEYNSASYEWTYPYWGQGTQVT VSSDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAK GQPREPQVYTLPPSREEMTKNQVSLTCLVKGFYPSDIAVEW ESNGQPENNYKTTPPVLDSDGSFFLYSKLTVDKSRWQQGNV FSCSVMHEALHNHYTQKSLSLSPGK | 58 | RBD |
| RBD10i10-Fc | QVQLQESGGGLVQAGGSLRLSCAASGTIFQVGSMGWYRQAP GKGRKFVATIADGGSTNYAGSVKGRFTISRDNAKNTVYLQM NSLKPEDTAVYYCAALGQVSEYNSASYEWTYPYWGQGTQVT VSSDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAK GQPREPQVYTLPPSREEMTKNQVSLTCLVKGFYPSDIAVEW ESNGQPENNYKTTPPVLDSDGSFFLYSKLTVDKSRWQQGNV FSCSVMHEALHNHYTQKSLSLSPGK | 59 | RBD |
| RBD10i14-Fc | QVQLQESGGGLVQAGGSLRLSCAASGTIFQVGSVGWYRQAP GKGRKFVATIADGSSTNYAGSVKGRFTISRDNAKNTVYLQM NSLKPEDTAVYYCAALGQVSEYNSASYEWTYPYWGQGTQVT VSSDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAK GQPREPQVYTLPPSREEMTKNQVSLTCLVKGFYPSDIAVEW ESNGQPENNYKTTPPVLDSDGSFFLYSKLTVDKSRWQQGNV FSCSVMHEALHNHYTQKSLSLSPGK | 60 | RBD |
| RBD11-Fc | QVQLQESGGGLVQAGGSLRLSCAASGNIFAKVWMGWYRQAP GKEREFVASIANGATTYYADSVKGRFTISRDNAKNTVYLQM NSLKPEDTAVYYCAARNWSGLGHFYWGQGTQVTVSSDKTHT CPPCPAPELLGGPSVFLFPPKPKDTLMISRTPEVTCVVVDV SHEDPEVKFNWYVDGVEVHNAKTKPREEQYNSTYRVVSVLT VLHQDWLNGKEYKCKVSNKALPAPIEKTISKAKGQPREPQV YTLPPSREEMTKNQVSLTCLVKGFYPSDIAVEWESNGQPEN NYKTTPPVLDSDGSFFLYSKLTVDKSRWQQGNVFSCSVMHE ALHNHYTQKSLSLSPGK | 61 | RBD |
| RBD11i12-Fc | QVQLQESGGGLVQAGGSLRLSCAASGNIFAKVWMGWYRQAP GKGREFVASIANGATTYYADSVKGRFTISRDNAKNTVYLQM NSLKPEDTAVYYCAARNWSGLGYFYWSQGTQVTVSSDKTHT CPPCPAPELLGGPSVFLFPPKPKDTLMISRTPEVTCVVVDV SHEDPEVKFNWYVDGVEVHNAKTKPREEQYNSTYRVVSVLT VLHQDWLNGKEYKCKVSNKALPAPIEKTISKAKGQPREPQV YTLPPSREEMTKNQVSLTCLVKGFYPSDIAVEWESNGQPEN NYKTTPPVLDSDGSFFLYSKLTVDKSRWQQGNVFSCSVMHE ALHNHYTQKSLSLSPGK | 62 | RBD |
| NbG1 | EVQLVESGGGLVQAGGSLRLSCAASGFTFSSYAMGWYRQAP GKEREFVAAISWSGGSTYYADSVKGRFTISRDNAKNTVYLQ MNSLKPEDTAVYYCARHWSARYWGQGTQVTVSS | 63 | GFP |
| NbG1i1 | EVQLVESGGGLVQAGGSLRLSCAASGFTFSSYAMGWYRQAP GKEREFVAAISWSGGSTYYADSVKGRFTISRDNAKNTVYLQ MNSLKPEDTAVYYYARHWSARYWGQGTQVTVSS | 64 | GFP |

REFERENCES

The following references are herein incorporated by reference in their entirety with the exception that, should the scope and meaning of a term conflict with a definition explicitly set forth herein, the definition explicitly set forth herein controls:

Feldhaus M J, et al., (2003) Nat Biotechnol 21:163-170.
Boder & Wittrup (1997) Nat Biotechnol 15:553-557.
Cherf & Cochran (2015) Methods Mol Biol 1319:155-175.
Ravikumar A, et al. (2014) Nat Chemical Biology 10:175-177.
Ravikumar A, et al. (2018) Cell 175:1946-1957.
Zhong Z, et al. (2018) ACS Synthetic Biology 7:2930-2934.
McMahon C, et al. (2018) Nature Struct Mol Biol 25:289-296.
Rakestraw J A, et al. (2009) Biotechnol Bioeng 103(6): 1192-1201.
Fitzgerald & Glick (2014) Microb Cell Fact 13: 125.

All scientific and technical terms used in this application have meanings commonly used in the art unless otherwise specified.

Except when specifically indicated, peptides are indicated with the N-terminus on the left and the sequences are written from the N-terminus to the C-terminus. Similarly, except when specifically indicated, nucleic acid sequences are indicated with the 5' end on the left and the sequences are written from 5' to 3'.

As used herein, a "parental sequence" refers to the initial sequence that is subjected to epOrthoRep. That is, the parental sequence refers to the sequence of the gene of interest provided on a P1 integration plasmid or the protein it encodes that is to be artificially evolved to have one or more desired characteristics. Although one or more sequences on the P1 integration plasmid that are provided for effecting orthogonal replication, surface display, selection, and/or detection may also be artificially evolved by way of being integrated on the P1 expression plasmid, such a sequence is not considered part of the parental sequence unless mutations in the sequence caused by epOrthoRep will be specifically selected over its original starting sequence.

As used herein, a "P1 plasmid" refers to a plasmid capable of orthogonal replication in yeast cells. P1 plasmids comprise recognition elements, which minimally include p1-specific terminal proteins (TPs) and terminal inverted repeats, that are needed for replication of a gene of interest by a TP-DNAP1.

As used herein, a "P1 integration plasmid" refers to a circular or linear plasmid that is used to insert a gene of interest into a P1 plasmid of a yeast cell by homologous recombination after transducing the yeast cell therewith.

As used herein, a "P1 expression plasmid" refers to the P1 plasmids of a yeast cell that have been modified to express a given parental sequence and copies thereof resulting from one or more epOrthoRep rounds.

As used herein, "P2 components" refers to the components encoded on naturally occurring P2 plasmids and derivatives thereof that are needed for orthogonal replication of P1 plasmids. One or more of the P2 components need not be encoded on a P2 plasmid, but may instead be encoded in the yeast host cell's nuclear DNA or in another plasmid (including P1 expression plasmids) found in the yeast host cell.

As used herein, a "secretory leader sequence" refers to a peptide (or, as the context dictates, the nucleic acid sequence encoding the peptide) that targets a protein fused thereto for secretion. See, e.g., Rakestraw J A, et al. (2009) and Fitzgerald & Glick (2014).

As used herein, an "attachment sequence" refers a peptide (or, as the context dictates, the nucleic acid sequence encoding the peptide) that is capable of being immobilized on the cell surface of a yeast host cell, whereby a protein fused to the attachment sequence will be immobilized on the cell surface when secreted thereto. Attachment sequences include SAG1, SED1, CWP2, AGA2, and Flo1p sequences and derivatives thereof.

As used herein, a "desired characteristic" refers to a structure or function that one desires a given protein to obtain that it does not already possess. Such desired characteristics include: affinity; selectivity; agonism; antagonism; inhibition; irreversible binding; enhancement; a different affinity, avidity, and/or specificity for a target the protein is already capable of binding; an ability to bind a new target; an ability to catalyze a given reaction it is already capable of catalyzing but with a different efficiency and/or under different reaction conditions; an ability to catalyze a new reaction that gives a new product or the same reaction product it already produces but by way of a different synthetic pathway; a change in its resistance or susceptibility to a given condition, e.g., heat, moisture, a given pH, a given chemical or other biomolecule (e.g., protease), degradation, agglutination; a change in a structural domain, a structural motif, a protein fold, and/or super secondary structure; and the like.

As used herein, an "affinity reagent" refers to a compound (e.g., an antibody or fragment thereof, a receptor, an enzyme, etc.) that specifically binds a given target (e.g., a compound or composition, a protein, a nucleic acid molecule, etc.), or vice versa. For example, an affinity reagent may an enzyme that binds with a protein substrate or the affinity reagent may be the protein substrate that binds with the enzyme.

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., (1990) J Mol Biol 215:403-410. Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences. Alternatively, the comparison window can exist over the full length of the sequences being compared. For purposes herein, where a given comparison window (e.g., over 80% of the given sequence) is not provided, the recited sequence identity is over 100% of the given sequence. Additionally, for the percentages of sequence identity of the proteins provided herein, the percentages are determined using BLASTP 2.8.0+, scoring matrix BLOSUM62, and the default parameters available at blast.ncbi.nlm.nih.gov/Blast.cgi. See also Altschul, et al., (1997) Nucleic Acids Res 25:3389-3402; and Altschul, et al., (2005) FEBS J 272: 5101-5109.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection.

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus.

Polypeptides may be made using methods known in the art including chemical synthesis, biosynthesis or in vitro synthesis using recombinant DNA methods, and solid phase synthesis. See, e.g., Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, IL, which are herein incorporated by reference. Polypeptides may be purified using protein purification techniques known in the art such as reverse phase high-performance liquid chromatography (HPLC), ion-exchange or immunoaffinity chromatography, filtration or size exclusion, or electrophoresis. See, e.g., Olsnes and Pihl (1973) Biochem. 12(16):3121-3126; and Scopes (1982) Protein Purification, Springer-Verlag, NY, which are herein incorporated by reference. Alternatively, the polypeptides may be made by recombinant DNA techniques known in the art.

As used herein, "antibody" refers to naturally occurring and synthetic immunoglobulin molecules and immunologically active portions thereof (i.e., molecules that contain an antigen binding site that specifically bind the molecule to which antibody is directed against, such as minibodies and nanobodies). As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include: single chain Fvs (scFvs), Fab fragments, Fab' fragments, F(ab')2, disulfide linked Fvs (sdFvs), Fvs, and fragments comprising or alternatively consisting of, either a VL or a VH domain.

As used herein, a compound (e.g., receptor or antibody) "specifically binds" a given target (e.g., ligand or epitope) if it reacts or associates more frequently, more rapidly, with greater duration, and/or with greater binding affinity with the given target than it does with a given alternative, and/or indiscriminate binding that gives rise to non-specific binding and/or background binding. As used herein, "non-specific binding" and "background binding" refer to an interaction that is not dependent on the presence of a specific structure (e.g., a given epitope). An example of a compound that specifically binds a given target is an antibody that binds its target antigen with greater affinity, avidity, more readily, and/or with greater duration than it does to other compounds. As used herein, an "epitope" is the part of a molecule that is recognized by an antibody. Epitopes may be linear epitopes or three-dimensional epitopes. As used herein, the terms "linear epitope" and "sequential epitope" are used interchangeably to refer to a primary structure of an antigen, e.g., a linear sequence of consecutive amino acid residues, that is recognized by an antibody. As used herein, the terms "three-dimensional epitope" and "conformational epitope" are used interchangeably to refer a three-dimensional structure that is recognized by an antibody, e.g., a plurality of non-linear amino acid residues that together form an epitope when a protein is folded.

As used herein, "binding affinity" refers to the propensity of a compound to associate with (or alternatively dissociate from) a given target and may be expressed in terms of its dissociation constant, Kd. In some embodiments, the antibodies have a Kd of $10^{-5}$ or less, $10^{-6}$ or less, preferably $10^{-7}$ or less, more preferably $10^{-8}$ or less, even more preferably $10^{-9}$ or less, and most preferably $10^{-10}$ or less, to their given target. Binding affinity can be determined using methods in the art, such as equilibrium dialysis, equilibrium binding, gel filtration, immunoassays, surface plasmon resonance, and spectroscopy using experimental conditions that exemplify the conditions under which the compound and the given target may come into contact and/or interact. Dissociation constants may be used determine the binding affinity of a compound for a given target relative to a specified alternative. Alternatively, methods in the art, e.g., immunoassays, in vivo or in vitro assays for functional activity, etc., may be used to determine the binding affinity of the compound for the given target relative to the specified alternative.

The use of the singular can include the plural unless specifically stated otherwise. As used in the specification and the appended claims, the singular forms "a", "an", and "the" can include plural referents unless the context clearly dictates otherwise.

As used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the phrase "one or more of", e.g., "one or more of A, B, and/or C" means "one or more of A", "one or more of B", "one or more of C", "one or more of A and one or more of B", "one or more of B and one or more of C", "one or more of A and one or more of C" and "one or more of A, one or more of B, and one or more of C".

The phrase "comprises or consists of A" is used as a tool to avoid excess page and translation fees and means that in some embodiments the given thing at issue: comprises A or consists of A. For example, the sentence "In some embodiments, the composition comprises or consists of A" is to be interpreted as if written as the following two separate sentences: "In some embodiments, the composition comprises A. In some embodiments, the composition consists of A."

Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C." As another example, the sentence "In some embodiments, the composition comprises at least A, B, or C" is to be interpreted as if written as the following three separate sentences: "In some embodiments, the composition comprises at least A. In some embodiments, the composition comprises at least B. In some embodiments, the composition comprises at least C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A P1 plasmid comprising
   (a) a constitutively active P1 promoter having SEQ ID NO: 2 or SEQ TD NO: 7,
   (b) a secretory leader sequence encoding SEQ ID NO: 6 or SEQ TD NO: 11,
   (c) an attachment sequence encoding SEQ ID NO: 1, and
   (d)(1) a polyA tail comprising at least 50 adenosine bases, 2) a self-cleaving ribozyme sequence encoding SEQ TD NO: 4, or both.

2. The P1 plasmid according claim 1, which further comprises a selection marker, a tag, or both for detecting protein expression.

3. The P1 plasmid according claim 2, wherein the selection marker is Trp1 and the tag is an HA tag.

4. The P1 plasmid according to claim 1, and further comprising a parental sequence or a backbone sequence into which the parental sequence is inserted.

5. The P1 plasmid according to claim 4, wherein the backbone sequence comprises SEQ ID NO: 10, wherein the region of Xaa's is any CDR3 sequence of interest.

6. The P1 plasmid according claim 1, wherein the P1 plasmid is a P1 expression plasmid or a P1 integration plasmid.

7. A kit comprising h P1 plasmid according claim 1 packaged together with; one or more reagents or devices for transducing a yeast cell therewith; or a yeast host cell comprising one or more or all P2 components for orthogonal replication of the P1 plasmid.

8. The kit according to claim 7, wherein the P1 plasmid comprises terminal proteins flanking a wildtype DNA polymerase that is endogenous to the terminal proteins and a selection marker.

9. The kit according to claim 8, wherein the P1 plasmid has SEQ ID NO: 8.

10. The kit according to claim 8, wherein the selection marker is Met15.

11. A yeast host cell comprising the P1 plasmid according to claim 1, optionally comprising an error prone DNA polymerase that replicates the P1 plasmid at an error rate above the average normal genomic error rate of the yeast host cell, and one or more or all P2 components for orthogonal replication the P1 plasmid.

12. A kit comprising the yeast host cell according to claim 11 packaged together with one or more reagents or devices for culturing and/or transducing the yeast host cell.

* * * * *

SEQUENCE LISTING

<160> NUMBER OF SEQ ID NOS: 66

<210> SEQ ID NO 1

-continued

```
<211> LENGTH: 74
<212> TYPE: PRT
<213> ORGANISM: Artificial Sequence
<220> FEATURE:
<223> OTHER INFORMATION: AGA2 attachment sequence

<400> SEQUENCE: 1

Met Gln Leu Leu Arg Cys Phe Ile Phe Val Ile Ala Val Leu Ala Gln
1               5                   10                  15

Glu Leu Thr Thr Ile Cys Glu Gln Ile Pro Pro Thr Leu Glu Thr Pro
            20                  25                  30

Tyr Leu Thr Thr Thr Ile Leu Ala Asn Gly Lys Ala Met Gln Gly Val
        35                  40                  45

Phe Glu Tyr Tyr Lys Val Thr Phe Val Asn Cys Gly His Pro Thr Thr
    50                  55                  60

Lys Gly Pro Ile Asn Thr Gln Tyr Val Phe
65                  70

<210> SEQ ID NO 2
<211> LENGTH: 100
<212> TYPE: DNA
<213> ORGANISM: Artificial Sequence
<220> FEATURE:
<223> OTHER INFORMATION: p10B2 promoter sequence

<400> SEQUENCE: 2
gatgacctat acataggaag atctatagaa acaaaaagat taataacttt caaatatcag      60
aaaaatgtag aaacatgtga taagctcata gacatgtaaa                           100

<210> SEQ ID NO 3
<211> LENGTH: 52
<212> TYPE: PRT
<213> ORGANISM: Artificial Sequence
<220> FEATURE:
<223> OTHER INFORMATION: Hammerhead ribozyme

<400> SEQUENCE: 3

Cys Cys Thr Gly Thr Cys Ala Cys Cys Gly Gly Ala Thr Gly Thr Gly
1               5                   10                  15

Thr Thr Thr Thr Cys Cys Gly Gly Thr Cys Thr Gly Ala Thr Gly Ala
            20                  25                  30

Gly Thr Cys Cys Gly Thr Gly Ala Gly Gly Ala Cys Gly Ala Ala Ala
        35                  40                  45

Cys Ala Gly Gly
    50

<210> SEQ ID NO 4
<211> LENGTH: 127
<212> TYPE: PRT
<213> ORGANISM: Artificial Sequence
<220> FEATURE:
<223> OTHER INFORMATION: AT110 nanobody

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Ala Asp
            20                  25                  30

Ile Met Gly Trp Tyr Arg Gln Ala Pro Gly Lys Glu Arg Glu Leu Val
        35                  40                  45

Ala Ser Ile Thr Asp Gly Gly Ser Thr Asn Tyr Ala Asp Ser Val Lys
```

```
                    50                  55                  60
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                     85                  90                  95

Ala Ile Ala Tyr Pro Asp Ile Pro Thr Tyr Phe Asp Tyr Asp Ser Asp
                    100                 105                 110

Tyr Phe Tyr Trp Gly Gln Gly Thr Gln Val Thr Val Ser Ser Ser
                115                 120                 125

<210> SEQ ID NO 5
<211> LENGTH: 366
<212> TYPE: PRT
<213> ORGANISM: Artificial Sequence
<220> FEATURE:
<223> OTHER INFORMATION: AT1R Angiotensin II type 1 receptor (AT1R)
      sequence

<400> SEQUENCE: 5

Asp Tyr Lys Asp Asp Asp Lys Ile Leu Asn Ser Ser Thr Glu Asp
 1               5                  10                  15

Gly Ile Lys Arg Ile Gln Asp Asp Cys Pro Lys Ala Gly Arg His Asn
                 20                  25                  30

Tyr Ile Phe Val Met Ile Pro Thr Leu Tyr Ser Ile Ile Phe Val Val
                 35                  40                  45

Gly Ile Phe Gly Asn Ser Leu Val Val Ile Val Ile Tyr Phe Tyr Met
             50                  55                  60

Lys Leu Lys Thr Val Ala Ser Val Phe Leu Leu Asn Leu Ala Leu Ala
 65                  70                  75                  80

Asp Leu Cys Phe Leu Leu Thr Leu Pro Leu Trp Ala Val Tyr Thr Ala
                 85                  90                  95

Met Glu Tyr Arg Trp Pro Phe Gly Asn Tyr Leu Cys Lys Ile Ala Ser
                100                 105                 110

Ala Ser Val Ser Phe Asn Leu Tyr Ala Ser Val Phe Leu Leu Thr Cys
             115                 120                 125

Leu Ser Ile Asp Arg Tyr Leu Ala Ile Val His Pro Met Lys Ser Arg
            130                 135                 140

Leu Arg Arg Thr Met Leu Val Ala Lys Val Thr Cys Ile Ile Ile Trp
145                 150                 155                 160

Leu Leu Ala Gly Leu Ala Ser Leu Pro Ala Ile Ile His Arg Asn Val
                165                 170                 175

Phe Phe Ile Glu Asn Thr Asn Ile Thr Val Cys Ala Phe His Tyr Glu
                180                 185                 190

Ser Gln Asn Ser Thr Leu Pro Ile Gly Leu Gly Leu Thr Lys Asn Ile
            195                 200                 205

Leu Gly Phe Leu Phe Pro Phe Leu Ile Ile Leu Thr Ser Tyr Thr Leu
        210                 215                 220

Ile Trp Lys Ala Leu Lys Lys Ala Tyr Glu Ile Gln Lys Asn Lys Pro
225                 230                 235                 240

Arg Asn Asp Asp Ile Phe Lys Ile Ile Met Ala Ile Val Leu Phe Phe
                245                 250                 255

Phe Phe Ser Trp Ile Pro His Gln Ile Phe Thr Phe Leu Asp Val Leu
            260                 265                 270

Ile Gln Leu Gly Ile Ile Arg Asp Cys Arg Ile Ala Asp Ile Val Asp
        275                 280                 285
```

```
Thr Ala Met Pro Ile Thr Ile Cys Ile Ala Tyr Phe Asn Asn Cys Leu
        290                 295                 300

Asn Pro Leu Phe Tyr Gly Phe Leu Gly Lys Lys Phe Lys Arg Tyr Phe
305                 310                 315                 320

Leu Gln Leu Leu Lys Tyr Ile Pro Pro Lys Ala Lys Ser His Ser Asn
                325                 330                 335

Leu Ser Thr Lys Met Ser Thr Leu Ser Tyr Arg Pro Ser Asp Asn Val
                340                 345                 350

Ser Ser Ser Thr Lys Lys Pro Ala Pro Cys Phe Glu Val Glu
                355                 360                 365

<210> SEQ ID NO 6
<211> LENGTH: 85
<212> TYPE: PRT
<213> ORGANISM: Artificial Sequence
<220> FEATURE:
<223> OTHER INFORMATION: App8 secretory leader sequence

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Ala Leu Pro Leu Ser Asn Ser Thr Asn Asn Gly Leu Ser
    50                  55                  60

Ser Thr Asn Thr Thr Ile Ala Ser Ile Ala Ala Lys Glu Glu Gly Val
65                  70                  75                  80

Gln Leu Asp Lys Arg
                85

<210> SEQ ID NO 7
<211> LENGTH: 100
<212> TYPE: DNA
<213> ORGANISM: Artificial Sequence
<220> FEATURE:
<223> OTHER INFORMATION: pGA promoter sequence

<400> SEQUENCE: 7
gatgacctat acataggaag atctatagaa acaaaaagat taataacttt caaatatcag      60
aaaaatatag aaacatgtga taagctcata gacatataaa                           100

<210> SEQ ID NO 8
<211> LENGTH: 5355
<212> TYPE: DNA
<213> ORGANISM: Artificial Sequence
<220> FEATURE:
<223> OTHER INFORMATION: Landing Pad plasmid sequence

<400> SEQUENCE: 8
acacataaca tagggggagag tactaaaagt gagattattg gaagattagt acgtctccat     60
ttttttctgt tttttttgttt ttatatatta ggttattttt tttcagtttt atatcaactc    120
tgtataacaa gtctattttt ttatattta agtctatttt acactttga cctataagtc      180 attttattat acacatttttc caactataat atatgaatta cattattaat ttaaaaatgg   240
attacaaaga taaggcttta aatgatctaa gaaatgtata tgccgacttt gattcacttc    300
ctttagattt tagacaaata ttaataaaag atagagccac acttcttcaa aaagaagatg   360
```

```
tagaaaagaa aatattggaa agacaagaag atgcaaagaa atatgcagaa tatttaaaac    420
aatcagaaat accagaacga atatctttgc ctaacattaa aagacataaa ggtgtttcta    480
tatcttttga agaaacatca gaagatatgg ttttggaacc aagacctttt attttttgatg   540 gattaaaatat tagatgtttt agacgagaga caattttctc tctcaaaaat aaaatattaa   600
acatggtaaa agaaagttct tcttttaaaa atgtttctag acaatcagtt tctttcatgt    660
attttaaaat ttttaataaa gggaaagtta tagcttctac aaaaagtgta aatatttatg    720
aagataaaat agatgagaga ttagaagatt tgtgtaataa ttttgacgat gtattaaaga    780
aaattataga tgtaacttat ggttatgaaa gtttatttgt ttcagaaaca tattcttatg    840
ttatatttta tgctaaatct atatatttcc ctcaacctag atgtgtgaat aattggggta    900
ataatattcc taatattctt actttcgata gttttaagct tttcacagct aataaaaata    960
atgtttcttg tattaaacag tgctctcgtt ttctgtggca aaaagatttt aatacattag   1020
aagaaatgat agaatataaa aatggtaata tttgtatagt tactcctcaa ttacatataa   1080
atgatgtaag agacataaaa tcatttaacg acatacgttt atattcagaa agtcctatta   1140
aaacattcag tgttatagat aatactataa catatttgtt ttattttaaa gaacatttag   1200
gagttatatt taatattact aaatccagac atgatagaag agtcactaaa tttagtcctt   1260
tgtcaaaatt ttctgatgtt aaaaatataa cagtatgttt tgatatagaa tcttattttg   1320
atccagaaaa agaatctaat caagttaata tacccttttat atgttgtgca tctataatat   1380
ataataaagt cataggaaat attgtagatt ttgaaggaag agattgtgta gctcaaatga   1440
tagaatatgt tgtagatata tgtggagagc ttaatatatc ttcagtggaa ctaattgcac   1500
ataatggtgg aggttatgat tttcattata ttttaagtag tatgtataat cctgcagcta   1560
ttaaaaatat attaattaga aataactcat ttataagttt taattttgct cacgatggag   1620
tcaaattttc tgtaaaagat tcctatagtt tcttgttatg tagtttagca aatgcttcaa   1680
aagcattttt aaacgaagaa acctttaaga aaacagattt tccccatcat gatttaaaaa   1740
cagcagatga tttatataaa gtatataaag aatggtcatc tgtaaacact gaaataaatc   1800
atgtagtgga aaaagaaaaa cttcttataa catcagaaca tatagttaat ttcactaaaa   1860
atgataaatc taaaactcta atagaatggt ctaaagatta ttgtagaaat gatgttttgg   1920
ttttatctaa ggtatggtta gaatttaaaa atgctgtaga agatatttt aattgtgaat   1980 tagtagatca aactatgaca ttagcaggac taagttataa attatttcaa gcaaatatgc   2040
cttttgatgt tgaattaaga catccaaata aagaagatta ttttaacatg agagaggctt   2100
taataggagg gagatgtatt agtgtcaatg gaatatataa agatgtttta tgtttagatg   2160
taaaatcatt atatccagca tctatggcat tttatgacca gccatatgga tctttcaaaa   2220
gagtatctag tagacctaaa gatgaattag gtatttatta tgtcagagta actcctaata   2280
gaaataataa atccaacttt ttccctataa gaagtcacaa taaaattact tataataatt   2340
ttgaagaaag tacatatata gcatggtata caaatgtaga tatagatata ggtttgtctg   2400
aaggtcataa tatagaatat atcccctttg attcttatgg aaatataggt tattcttggt   2460
ctaaaaaagg taaatattc gaaaatatata taaaagacgt gctgtacaaa ttaaaaataa   2520
agtatgaaaa acaaaacaat aaagttaaaa gaaatgttat caaattatt atgaacagtt   2580 tatggggcaa attcgcacaa aaatgggtaa attttgagta ttttataaaa tcagaagatg   2640
atatagattt tgagtcagaa gaggcatata agatatggga cactgatttt atgctgataaa   2700 agaaaattaa agaatctact tattcatcta aacctataca aaatggagta tttacattaa   2760
```

```
gttgggcaag ataccacatg aaaagtatat gggatgcagg ggctaaagaa ggagcagaat    2820
gtatctattc ggacacagat agtattttg tacataaaga acattttaaa aagaatgcta    2880
aatttatgtt aaatggttta aaagttccta ttataggatc agaagtagga caattagaat    2940
tagaatgtga gtttgataaa ttgttatgtg caggtaaaaa gcaatacatg ggattttata    3000
cttattttca agatggaaaa ccatgtataa aagaaaagaa aagatttaag ggtattccta    3060
gtaattatat aatacctgaa ttatatgctc atttactttc aggtgcagac aaagaagcta    3120
aaatacaatt tttgaaattt agaagagaat ggggatcagt taaaggatat atagaaaata    3180
agaccgtgaa agctacttaa gatcttgtat agataaaaaa ttacgtatat catttataga    3240
tggagaagtt aataaatttt ctaaaagagg aaaattaatt tctaatgtga acactagtga    3300
gatagctaaa gatcttaatt gtgaaaacaa tattgaaagt ataataaata cattaaaaga    3360
acaaaataga tattttgaca aacaaattgc atatgccatc tcatttcgat actgttcaac    3420
tacacgccgg ccaagagaac cctggtgaca atgctcacag atccagagct gtaccaattt    3480
acgccaccac ttcttatgtt ttcgaaaact ctaagcatgg ttcgcaattg tttggtctag    3540
aagttccagg ttacgtctat tcccgttttcc aaaacccaac cagtaatgtt ttggaagaaa    3600
gaattgctgc tttagaaggt ggtgctgctg ctttggctgt ttcctccggt caagccgctc    3660
aaacccttgc catccaaggt ttggcacaca ctggtgacaa catcgtttcc acttcttact    3720
tatacggtgg tacttataac cagttcaaaa tctcgttcaa aagatttggt atcgaggcta    3780
gatttgttga aggtgacaat ccagaagaat tcgaaaaggt ctttgatgaa agaaccaagg    3840
ctgtttattt ggaaaccatt ggtaatccaa agtacaatgt tccggatttt gaaaaaattg    3900
ttgcaattgc tcacaaacac ggtattccag ttgtcgttga caacacattt ggtgccggtg    3960
gttacttctg tcagccaatt aaatacggtg ctgatattgt aacacattct gctaccaaat    4020
ggattggtgg tcatggtact actatcggtg gtattattgt tgactctggt aagttcccat    4080
ggaaggacta cccagaaaag ttccctcaat tctctcaacc tgccgaagga tatcacggta    4140
ctatctacaa tgaagcctac ggtaacttgg catacatcgt tcatgttaga actgaactat    4200
taagagattt gggtccattg atgaacccat ttgcctcttt cttgctacta caaggtgttg    4260
aaacattatc tttgagagct gaaagacacg gtgaaaatgc attgaagtta gccaaatggt    4320
tagaacaatc cccatacgta tcttgggttt catacccttgg tttagcatct cattctcatc    4380
atgaaaatgc taagaagtat ctatctaacg gttcggtgg tgtcttatct ttcggtgtaa    4440
aagacttacc aaatgccgac aaggaaactg acccattcaa actttctggt gctcaagttg    4500
ttgacaattt aaagcttgcc tctaacttgg ccaatgttgg tgatgccaag accttagtca    4560
ttgctccata cttcactacc cacaaacaat taaatgacaa agaaaagttg gcatctggtg    4620
ttaccaagga cttaattcgt gtctctgttg gtatcgaatt tattgatgac attattgcag    4680
acttccagca atccttttgaa actgttttcg ctggccaaaa accatgaaaa actgtattat    4740
aagtaaatgc aggtatacta aactcacaaa ttagagcttc aatttaatta tatcagttat    4800
tacccgagct ccgttttctat tatgaatttc atttataaag tttatgtaca aatatcataa    4860
aaaaagagaa tctttggatc cagagatata aaatttaata tggaaaaaat aagacaagaa    4920
agatacaacc aaatgaaaga agctctaaat agtgttgaag gttataaagg aaaaattgta    4980
gcctcagact cagattggtg tttcaaagat cctcaaggca atagaataac agattttgat    5040
agtattaata aagaattagg tcttggtaga agagatgtaa aattagataa aggtcatgat    5100
```

```
gatttaatta aattatgtac tgaaaaaata gatagtatga ataatctaca gaatggaaaa    5160
tgtgtataat aaaatgactt ataggtcaaa agtgtaaaat agacttaaaa tataaaaaaa    5220
tagacttgtt atacagagtt gatataaaac tgaaaaaaaa taacctaata tataaaaaca    5280
aaaaaacaga aaaaaatgga gacgtactaa tcttccaata atctcacttt tagtactctc    5340
ccctatgtta tgtgt                                                     5355

<210> SEQ ID NO 9
<211> LENGTH: 9
<212> TYPE: PRT
<213> ORGANISM: Artificial Sequence
<220> FEATURE:
<223> OTHER INFORMATION: HA tag

<400> SEQUENCE: 9

Tyr Pro Tyr Asp Val Pro Asp Tyr Ala
1               5

<210> SEQ ID NO 10
<211> LENGTH: 112
<212> TYPE: PRT
<213> ORGANISM: Artificial Sequence
<220> FEATURE:
<223> OTHER INFORMATION: CDR3 nanobody construct
<220> FEATURE:
<221> NAME/KEY: misc_feature
<222> LOCATION: (97)..(102)
<223> OTHER INFORMATION: Xaa can be any naturally occurring amino acid

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Ser Tyr
            20                  25                  30

Ala Met Gly Trp Tyr Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Xaa Xaa Xaa Xaa Xaa Xaa Gly Gln Gly Thr Gln Val Thr Val Ser Ser
            100                 105                 110

<210> SEQ ID NO 11
<211> LENGTH: 85
<212> TYPE: PRT
<213> ORGANISM: Artificial Sequence
<220> FEATURE:
<223> OTHER INFORMATION: App8il secretory leader sequence

<400> SEQUENCE: 11

Met Arg Phe Pro Ser Ile Phe Thr Ala Ala Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Ala Leu Pro Leu Ser Asn Ser Thr Asn Asn Gly Leu Ser
    50                  55                  60
```

```
Ser Thr Asn Thr Thr Ile Ala Ser Ile Ala Ala Lys Glu Glu Gly Val
 65                  70                  75                  80

Gln Leu Asp Lys Arg
                85

<210> SEQ ID NO 12
<211> LENGTH: 127
<212> TYPE: PRT
<213> ORGANISM: Artificial Sequence
<220> FEATURE:
<223> OTHER INFORMATION: AT110i101 nanobody

<400> SEQUENCE: 12

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Asn Ile Phe Asp Ala Asp
                 20                  25                  30

Ile Met Gly Trp Tyr Arg Gln Ala Pro Gly Lys Glu Arg Glu Leu Val
             35                  40                  45

Ala Ser Ile Thr Asp Gly Gly Ser Thr Asn Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Val Ala Tyr Pro Asp Ile Pro Thr Tyr Phe Asp Tyr Asp Ser Asp
            100                 105                 110

Tyr Phe Tyr Trp Gly Gln Gly Thr Gln Val Thr Val Ser Ser
            115                 120                 125

<210> SEQ ID NO 13
<211> LENGTH: 127
<212> TYPE: PRT
<213> ORGANISM: Artificial Sequence
<220> FEATURE:
<223> OTHER INFORMATION: AT110i102 nanobody

<400> SEQUENCE: 13

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Asn Ile Phe Asp Ala Asp
                 20                  25                  30

Ile Met Gly Trp Tyr Arg Gln Ala Pro Gly Lys Glu Arg Glu Leu Val
             35                  40                  45

Ala Ser Ile Thr Asp Gly Gly Ser Thr Asn Tyr Ala Asp Ser Val Lys
         50                  55                  60

Gly His Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Val Ala Tyr Pro Asp Ile Pro Thr Tyr Phe Asp Tyr Asp Ser Asp
            100                 105                 110

Tyr Phe Tyr Trp Gly Gln Gly Thr Gln Val Thr Val Ser Ser
            115                 120                 125

<210> SEQ ID NO 14
<211> LENGTH: 127
<212> TYPE: PRT
```

<213> ORGANISM: Artificial Sequence
<220> FEATURE:
<223> OTHER INFORMATION: AT110i103 nanobody

<400> SEQUENCE: 14

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Ala Asp
            20                  25                  30

Ile Met Gly Trp Tyr Arg Gln Ala Pro Gly Lys Glu Arg Glu Leu Val
        35                  40                  45

Ala Ser Ile Thr Asp Gly Gly Ser Thr Asn Tyr Ala Asp Ser Val Lys
    50                  55                  60

Gly His Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Val Ala Tyr Pro Asp Ile Pro Thr Tyr Phe Asp Tyr Asp Ser Asp
            100                 105                 110

His Phe Tyr Trp Gly Gln Gly Thr Gln Val Thr Val Ser Ser Ser
        115                 120                 125
```

<210> SEQ ID NO 15
<211> LENGTH: 127
<212> TYPE: PRT
<213> ORGANISM: Artificial Sequence
<220> FEATURE:
<223> OTHER INFORMATION: AT110i104 nanobody

<400> SEQUENCE: 15

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Ala Asp
            20                  25                  30

Ile Met Gly Trp Tyr Arg Gln Ala Pro Gly Lys Glu Arg Glu Leu Val
        35                  40                  45

Ala Ser Ile Thr Asp Gly Gly Ser Thr Asn Tyr Ala Asp Ser Val Lys
    50                  55                  60

Gly His Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ile Ala Tyr Pro Asp Ile Pro Thr Tyr Phe Asp Tyr Asp Ser Asp
            100                 105                 110

Tyr Phe Tyr Trp Gly Gln Gly Thr Gln Val Thr Val Ser Ser Ser
        115                 120                 125
```

<210> SEQ ID NO 16
<211> LENGTH: 127
<212> TYPE: PRT
<213> ORGANISM: Artificial Sequence
<220> FEATURE:
<223> OTHER INFORMATION: AT110i105 nanobody

<400> SEQUENCE: 16

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Ala Asp
            20                  25                  30
```

```
Ile Met Gly Trp Tyr Arg Gln Ala Pro Gly Lys Glu Arg Glu Leu Val
            35                  40                  45

Ala Ser Ile Thr Asp Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                85                  90                  95

Ala Ile Ala Tyr Pro Asp Ile Pro Thr Tyr Phe Asp Tyr Asp Ser Asp
                100                 105                 110

Tyr Phe His Trp Gly Gln Gly Thr Gln Val Thr Val Ser Ser
            115                 120                 125

<210> SEQ ID NO 17
<211> LENGTH: 118
<212> TYPE: PRT
<213> ORGANISM: Artificial Sequence
<220> FEATURE:
<223> OTHER INFORMATION: Nb.b201 nanobody

<400> SEQUENCE: 17

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Tyr Ile Ser Asp Ala Tyr
                20                  25                  30

Tyr Met Gly Trp Tyr Arg Gln Ala Pro Gly Lys Glu Arg Glu Phe Val
            35                  40                  45

Ala Thr Ile Thr His Gly Thr Asn Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Tyr Ser Leu Lys Pro Glu Asp Thr Ala Val Tyr Tyr Cys Ala
                85                  90                  95

Val Leu Glu Thr Arg Ser Tyr Ser Phe Arg Tyr Trp Gly Gln Gly Thr
                100                 105                 110

Gln Val Thr Val Ser Ser
            115

<210> SEQ ID NO 18
<211> LENGTH: 118
<212> TYPE: PRT
<213> ORGANISM: Artificial Sequence
<220> FEATURE:
<223> OTHER INFORMATION: Nb.b201i1 nanobody

<400> SEQUENCE: 18

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Tyr Ile Ser Asp Ala Tyr
                20                  25                  30

Tyr Met Gly Trp Tyr Arg Gln Ala Pro Gly Lys Glu Arg Gly Phe Val
            35                  40                  45

Ala Thr Ile Thr His Gly Thr Asn Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
```

```
                85                  90                  95
Val Leu Glu Thr Arg Ser Tyr Ser Phe Arg Tyr Trp Gly Gln Gly Thr
            100                 105                 110

Gln Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Nb.b201i3 nanobody

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Asp Ala Tyr
            20                  25                  30

Tyr Met Gly Trp Tyr Arg Gln Ala Pro Gly Lys Glu Arg Glu Phe Val
        35                  40                  45

Ala Thr Ile Thr His Gly Thr Asn Thr Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Leu Glu Thr Arg Ser Tyr Ser Phe Arg Tyr Trp Gly Gln Gly Thr
            100                 105                 110

Gln Val Thr Val Ser Ser
        115

<210> SEQ ID NO 20
<211> LENGTH: 122
<212> TYPE: PRT
<213> ORGANISM: Artificial Sequence
<220> FEATURE:
<223> OTHER INFORMATION: Lag42 nanobody

<400> SEQUENCE: 20

Met Ala Asp Val Gln Leu Val Glu Ser Gly Gly Gly Leu Val Gln Ala
1               5                   10                  15

Gly Asp Ser Leu Arg Leu Ser Cys Ala Ala Ser Gly Pro Thr Gly Ala
            20                  25                  30

Met Ala Trp Phe His Gln Gly Leu Gly Lys Glu Arg Glu Phe Val Gly
        35                  40                  45

Gly Ile Ser Pro Ser Gly Asp Asn Ile Tyr Tyr Ala Asp Ser Val Lys
50                  55                  60

Gly Arg Phe Thr Ile Asp Arg Asp Asn Ala Lys Asn Thr Val Ser Leu
65                  70                  75                  80

Gln Met Asn Ser Leu Lys Pro Glu Asp Met Gly Val Tyr Tyr Cys Ala
                85                  90                  95

Ala Arg Arg Arg Val Thr Leu Phe Thr Ser Arg Thr Asp Tyr Glu Phe
            100                 105                 110

Trp Gly Arg Gly Thr Gln Val Thr Val Ser
        115                 120

<210> SEQ ID NO 21
<211> LENGTH: 122
```

```
<212> TYPE: PRT
<213> ORGANISM: Artificial Sequence
<220> FEATURE:
<223> OTHER INFORMATION: Lag42i2 nanobody

<400> SEQUENCE: 21

Met Ala Asp Val Gln Leu Val Glu Ser Gly Gly Gly Leu Val Gln Ala
1               5                   10                  15

Gly Asp Ser Leu Arg Leu Ser Cys Ala Ala Ser Gly Pro Thr Gly Ala
            20                  25                  30

Met Ala Trp Phe His Gln Gly Leu Gly Lys Glu Arg Glu Phe Val Gly
        35                  40                  45

Gly Ile Ser Pro Ser Gly Asp Asp Ile Tyr Tyr Ala Asp Ser Val Lys
    50                  55                  60

Gly Arg Phe Thr Ile Asp Arg Asp Asn Ala Lys Asn Thr Val Ser Leu
65                  70                  75                  80

Gln Met Asn Ser Leu Lys Pro Glu Asp Met Gly Val Tyr Tyr Cys Ala
                85                  90                  95

Ala Arg Arg Arg Val Thr Leu Phe Thr Ser Arg Thr Asp Tyr Glu Phe
            100                 105                 110

Trp Gly Arg Gly Thr Gln Val Thr Val Ser
        115                 120

<210> SEQ ID NO 22
<211> LENGTH: 122
<212> TYPE: PRT
<213> ORGANISM: Artificial Sequence
<220> FEATURE:
<223> OTHER INFORMATION: Lag42i11 nanobody

<400> SEQUENCE: 22

Met Ala Asp Val Gln Leu Val Glu Ser Gly Gly Gly Leu Val Gln Ala
1               5                   10                  15

Gly Asp Ser Leu Arg Leu Ser Cys Ala Ala Ser Gly Pro Thr Gly Ala
            20                  25                  30

Met Ala Trp Phe His Gln Gly Leu Gly Lys Glu Arg Glu Phe Val Gly
        35                  40                  45

Gly Ile Ser Pro Ser Gly Asp Asp Ile Tyr Tyr Ala Asp Ser Val Lys
    50                  55                  60

Gly Arg Phe Thr Ile Asp Arg Asp Asn Ala Lys Asn Thr Val Ser Leu
65                  70                  75                  80

Gln Met Asn Ser Leu Lys Pro Glu Asp Met Gly Val Tyr Tyr Cys Ala
                85                  90                  95

Ala Arg Arg Arg Val Thr Leu Phe Thr Ser Arg Thr Asp Tyr Gly Phe
            100                 105                 110

Trp Gly Arg Gly Thr Gln Val Thr Val Ser
        115                 120

<210> SEQ ID NO 23
<211> LENGTH: 118
<212> TYPE: PRT
<213> ORGANISM: Artificial Sequence
<220> FEATURE:
<223> OTHER INFORMATION: RBD1 nanobody

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Glu Asn
```

```
            20                  25                  30

Phe Met Gly Trp Tyr Arg Gln Ala Pro Gly Lys Glu Arg Glu Leu Val
        35                  40                  45

Ala Gly Ile Asn Asp Gly Thr Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Ile Gly Thr Ser Val Leu Gly His Ala Tyr Trp Gly Gln Gly Thr
            100                 105                 110

Gln Val Thr Val Ser Ser
            115

<210> SEQ ID NO 24
<211> LENGTH: 118
<212> TYPE: PRT
<213> ORGANISM: Artificial Sequence
<220> FEATURE:
<223> OTHER INFORMATION: RBD1i1 nanobody

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Glu Asn
            20                  25                  30

Phe Met Gly Trp Tyr Arg Gln Ala Pro Gly Lys Glu Arg Lys Leu Val
        35                  40                  45

Ala Gly Ile Asn Asp Gly Thr Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Ile Gly Ala Ser Val Leu Gly His Ala Tyr Trp Gly Gln Gly Thr
            100                 105                 110

Gln Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: RBD1i13 nanobody

<400> SEQUENCE: 25

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Glu Asn
            20                  25                  30

Phe Met Gly Trp Tyr Arg Gln Ala Pro Gly Lys Gly Arg Lys Leu Val
        35                  40                  45

Ala Gly Ile Asn Asp Gly Thr Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80
```

```
Gln Met Asn Ser Leu Glu Pro Glu Asp Thr Ala Val Tyr Tyr Cys Ala
            85                  90                  95

Val Ile Gly Ala Ser Val Leu Gly His Ala Tyr Trp Gly Gln Gly Thr
        100                 105                 110

Gln Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: RBD3 nanobody

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
            20                  25                  30

Phe Met Gly Trp Tyr Arg Gln Ala Pro Gly Lys Glu Arg Glu Leu Val
        35                  40                  45

Ala Ala Ile Gly Arg Gly Ser Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Arg Asn Ala Thr Tyr Pro Tyr Val Tyr Trp Gly Gln Gly Thr
        100                 105                 110

Gln Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: RBD3i2 nanobody

<400> SEQUENCE: 27

Gln Ala Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
            20                  25                  30

Phe Met Gly Trp Tyr Arg Gln Ala Pro Gly Lys Glu Arg Glu Leu Val
        35                  40                  45

Ala Ala Ile Gly Arg Gly Ser Asn Thr Arg Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Arg Asn Ala Thr Tyr Pro Tyr Val Tyr Trp Gly Gln Gly Thr
        100                 105                 110

Gln Val Thr Val Ser Ser
        115

<210> SEQ ID NO 28
```

```
<211> LENGTH: 118
<212> TYPE: PRT
<213> ORGANISM: Artificial Sequence
<220> FEATURE:
<223> OTHER INFORMATION: RBD3i17 nanobody

<400> SEQUENCE: 28

Gln Ala Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
            20                  25                  30

Phe Met Gly Trp Tyr Arg Gln Ala Pro Gly Lys Glu Arg Glu Leu Val
        35                  40                  45

Ala Ala Ile Gly Arg Gly Ser Asn Thr Arg Cys Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asn Ala Thr Tyr Pro Tyr Tyr Val Tyr Trp Gly Gln Gly Thr
            100                 105                 110

Gln Val Thr Val Ser Ser
        115

<210> SEQ ID NO 29
<211> LENGTH: 122
<212> TYPE: PRT
<213> ORGANISM: Artificial Sequence
<220> FEATURE:
<223> OTHER INFORMATION: RBD6 nanobody

<400> SEQUENCE: 29

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Thr Thr Tyr
            20                  25                  30

Leu Met Gly Trp Tyr Arg Gln Ala Pro Gly Lys Glu Arg Glu Phe Val
        35                  40                  45

Ala Thr Ile Asn Arg Gly Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Asp Tyr Gly Leu Ala Tyr His Arg Tyr Trp
            100                 105                 110

Gly Gln Gly Thr Gln Val Thr Val Ser Ser
        115                 120

<210> SEQ ID NO 30
<211> LENGTH: 122
<212> TYPE: PRT
<213> ORGANISM: Artificial Sequence
<220> FEATURE:
<223> OTHER INFORMATION: RBD6id nanobody

<400> SEQUENCE: 30

Gln Val Gln Leu Gln Glu Ser Gly Gly Gly Leu Val Gln Ala Gly Gly
1               5                   10                  15
```

```
Ser Leu Arg Leu Asn Cys Ala Ala Asn Gly Ser Ile Ser Thr Thr Tyr
            20                  25                  30

Leu Met Gly Trp Tyr Arg Gln Ala Pro Gly Lys Glu Arg Glu Phe Val
        35                  40                  45

Ala Thr Ile Asn Arg Gly Gly Ser Thr Tyr Tyr Ala Ile Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Asp Tyr Gly Leu Ala Tyr His Arg Tyr Trp
            100                 105                 110

Gly Gln Gly Thr Gln Val Thr Val Ser Ser
            115                 120
```

<210> SEQ ID NO 31
<211> LENGTH: 122
<212> TYPE: PRT
<213> ORGANISM: Artificial Sequence
<220> FEATURE:
<223> OTHER INFORMATION: RBD6i10 nanobody

<400> SEQUENCE: 31

```
Gln Val Gln Leu Gln Glu Ser Gly Gly Gly Leu Val Gln Ala Gly Gly
1               5                   10                  15

Ser Leu Arg Leu Asn Cys Ala Ala Ser Gly Ser Ile Ser Thr Thr Tyr
            20                  25                  30

Leu Met Gly Trp Tyr Arg Gln Ala Pro Gly Lys Glu Arg Lys Phe Val
        35                  40                  45

Ala Thr Ile Asn Arg Gly Gly Ser Thr Tyr Tyr Ala Val Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Asp Tyr Gly Leu Ala Tyr His Arg Tyr Trp
            100                 105                 110

Gly Gln Gly Thr Gln Val Thr Val Asn Ser
            115                 120
```

<210> SEQ ID NO 32
<211> LENGTH: 122
<212> TYPE: PRT
<213> ORGANISM: Artificial Sequence
<220> FEATURE:
<223> OTHER INFORMATION: RBD6i13 nanobody

<400> SEQUENCE: 32

```
Gln Val Gln Leu Gln Glu Ser Gly Gly Gly Leu Val Gln Ala Gly Gly
1               5                   10                  15

Ser Leu Arg Leu Asn Cys Ala Ala Ser Gly Ser Ile Ser Thr Thr Tyr
            20                  25                  30

Leu Met Gly Trp Tyr Arg Gln Ala Pro Gly Lys Glu Arg Lys Phe Val
        35                  40                  45

Ala Thr Ile Asn Arg Gly Gly Ser Thr Tyr Tyr Ala Val Ser Val Lys
    50                  55                  60

Gly Arg Phe Thr Ile Ser Arg Asp Asn Ala Lys Asn Thr Val Tyr Leu
65                  70                  75                  80
```

Gln Met Asn Ser Leu Lys Pro Glu Asp Thr Ala Val Tyr Tyr Cys Ala
                85                  90                  95

Val Gly Trp Pro Asp Pro Gly Tyr Gly Leu Ala Tyr His Arg Tyr Trp
            100                 105                 110

Gly Gln Gly Thr Gln Val Thr Val Asn Ser
            115                 120

<210> SEQ ID NO 33
<211> LENGTH: 121
<212> TYPE: PRT
<213> ORGANISM: Artificial Sequence
<220> FEATURE:
<223> OTHER INFORMATION: RBD7 nanobody

<400> SEQUENCE: 33

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Glu Phe Val
            35                  40                  45

Ala Gly Ile Gly Gly Gly Ser Thr Asn Tyr Ala Asp Ser Val Lys Gly
        50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Arg Gly Tyr Phe Ser Tyr Trp Gly
            100                 105                 110

Gln Gly Thr Gln Val Thr Val Ser Ser
            115                 120

<210> SEQ ID NO 34
<211> LENGTH: 121
<212> TYPE: PRT
<213> ORGANISM: Artificial Sequence
<220> FEATURE:
<223> OTHER INFORMATION: RBD7i12 nanobody

<400> SEQUENCE: 34

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Glu Phe Val
            35                  40                  45

Ala Gly Ile Gly Gly Gly Ser Thr Asn Tyr Ala Asp Ser Val Lys Gly
        50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Cys Arg Gly Tyr Phe Ser Tyr Trp Gly
            100                 105                 110

Gln Gly Thr Gln Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: RBD7i13 nanobody

<400> SEQUENCE: 35

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Lys Phe Val
        35                  40                  45

Ala Gly Ile Gly Gly Gly Ser Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Cys Arg Gly Tyr Phe Ser Tyr Trp Gly
            100                 105                 110

Gln Gly Thr Gln Val Thr Val Ser Ser
            115                 120
```

<210> SEQ ID NO 36
<211> LENGTH: 118
<212> TYPE: PRT
<213> ORGANISM: Artificial Sequence
<220> FEATURE:
<223> OTHER INFORMATION: RBD8 nanobody

<400> SEQUENCE: 36

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gly Gly Pro
            20                  25                  30

Trp Met Gly Trp Tyr Arg Gln Ala Pro Gly Lys Glu Arg Glu Phe Val
        35                  40                  45

Ala Ala Ile Ala Arg Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asp Ala Val Tyr Pro Tyr Leu Lys Tyr Trp Gly Gln Gly Thr
            100                 105                 110

Gln Val Thr Val Ser Ser
        115
```

<210> SEQ ID NO 37
<211> LENGTH: 118
<212> TYPE: PRT
<213> ORGANISM: Artificial Sequence
<220> FEATURE:
<223> OTHER INFORMATION: RBD8i1 nanobody

<400> SEQUENCE: 37

```
Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Thr Ile Ser Gly Gly Pro
            20                  25                  30

Trp Met Gly Trp Tyr Arg Gln Ala Pro Gly Lys Glu Arg Glu Phe Val
            35                  40                  45

Ala Ala Ile Ala Arg Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asp Ala Val Tyr Pro Tyr Leu Lys Tyr Trp Gly Gln Gly Thr
            100                 105                 110

Gln Val Thr Val Ser Ser
            115

<210> SEQ ID NO 38
<211> LENGTH: 126
<212> TYPE: PRT
<213> ORGANISM: Artificial Sequence
<220> FEATURE:
<223> OTHER INFORMATION: RBD9 nanobody

<400> SEQUENCE: 38

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Tyr Ser Arg
            20                  25                  30

Arg Met Gly Trp Tyr Arg Gln Ala Pro Gly Lys Glu Arg Glu Phe Val
            35                  40                  45

Ala Thr Ile Gly His Gly Thr Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Pro Arg Pro His Gly Ala Gly Thr Ala Asp Ala Arg Tyr Asn
            100                 105                 110

Leu Trp Tyr Trp Gly Gln Gly Thr Gln Val Thr Val Ser Ser
            115                 120                 125

<210> SEQ ID NO 39
<211> LENGTH: 126
<212> TYPE: PRT
<213> ORGANISM: Artificial Sequence
<220> FEATURE:
<223> OTHER INFORMATION: RBD9i10 nanobody

<400> SEQUENCE: 39

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Phe Tyr Ser Arg
            20                  25                  30

Arg Met Gly Trp Tyr Arg Gln Ala Pro Gly Lys Glu Arg Glu Phe Val
            35                  40                  45

Ala Thr Ile Gly His Gly Ala Ser Thr Tyr Tyr Ala Gly Ser Val Lys
    50                  55                  60

Gly Arg Phe Thr Ile Ser Arg Asp Asn Ala Lys Asn Thr Val Tyr Leu

```
                65                  70                  75                  80
Gln Met Asp Ser Leu Lys Pro Glu Asp Thr Ala Val Tyr Tyr Cys Ala
                85                  90                  95

Ala Leu Pro Arg Pro His Gly Ala Gly Thr Ala Asp Ala Arg Tyr Asn
            100                 105                 110

Leu Trp Tyr Trp Gly Gln Gly Thr Gln Val Thr Val Ser Ser
        115                 120                 125

<210> SEQ ID NO 40
<211> LENGTH: 126
<212> TYPE: PRT
<213> ORGANISM: Artificial Sequence
<220> FEATURE:
<223> OTHER INFORMATION: RBD10 nanobody

<400> SEQUENCE: 40

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Met Gly Trp Tyr Arg Gln Ala Pro Gly Lys Glu Arg Glu Phe Val
        35                  40                  45

Ala Thr Ile Ala Asp Gly Ser Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser
        115                 120                 125

<210> SEQ ID NO 41
<211> LENGTH: 126
<212> TYPE: PRT
<213> ORGANISM: Artificial Sequence
<220> FEATURE:
<223> OTHER INFORMATION: RBD10i10 nanobody

<400> SEQUENCE: 41

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Met Gly Trp Tyr Arg Gln Ala Pro Gly Lys Gly Arg Lys Phe Val
        35                  40                  45

Ala Thr Ile Ala Asp Gly Gly Ser Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser
        115                 120                 125
```

```
<210> SEQ ID NO 42
<211> LENGTH: 126
<212> TYPE: PRT
<213> ORGANISM: Artificial Sequence
<220> FEATURE:
<223> OTHER INFORMATION: RBD10i14 nanobody

<400> SEQUENCE: 42

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Val Gly Trp Tyr Arg Gln Ala Pro Gly Lys Gly Arg Lys Phe Val
        35                  40                  45

Ala Thr Ile Ala Asp Gly Ser Ser Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser
        115                 120                 125

<210> SEQ ID NO 43
<211> LENGTH: 118
<212> TYPE: PRT
<213> ORGANISM: Artificial Sequence
<220> FEATURE:
<223> OTHER INFORMATION: RBD11 nanobody

<400> SEQUENCE: 43

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Lys Val
            20                  25                  30

Trp Met Gly Trp Tyr Arg Gln Ala Pro Gly Lys Glu Arg Glu Phe Val
        35                  40                  45

Ala Ser Ile Ala Asn Gly Ala Thr Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asn Trp Ser Gly Leu Gly His Phe Tyr Trp Gly Gln Gly Thr
            100                 105                 110

Gln Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: RBD11i12 nanobody

<400> SEQUENCE: 44

Gln Val Gln Leu Gln Glu Ser Gly Gly Gly Leu Val Gln Ala Gly Gly
```

```
            1               5                  10                 15
          Ser Leu Arg Leu Ser Cys Ala Ala Ser Gly Asn Ile Phe Ala Lys Val
                        20                  25                  30

Trp Met Gly Trp Tyr Arg Gln Ala Pro Gly Lys Gly Arg Glu Phe Val
                        35                  40                  45

Ala Ser Ile Ala Asn Gly Ala Thr Thr Tyr Tyr Ala Asp Ser Val Lys
                        50                  55                  60

Gly Arg Phe Thr Ile Ser Arg Asp Asn Ala Lys Asn Thr Val Tyr Leu
          65                          70                  75                  80

Gln Met Asn Ser Leu Lys Pro Glu Asp Thr Ala Val Tyr Tyr Cys Ala
                        85                  90                  95

Ala Arg Asn Trp Ser Gly Leu Gly Tyr Phe Tyr Trp Ser Gln Gly Thr
                        100                 105                 110

Gln Val Thr Val Ser Ser
                        115

<210> SEQ ID NO 45
<211> LENGTH: 345
<212> TYPE: PRT
<213> ORGANISM: Artificial Sequence
<220> FEATURE:
<223> OTHER INFORMATION: RBD1-Fc nanobody

<400> SEQUENCE: 45

Gln Val Gln Leu Gln Glu Ser Gly Gly Gly Leu Val Gln Ala Gly Gly
          1               5                   10                  15

Ser Leu Arg Leu Ser Cys Ala Ala Ser Gly Thr Ile Ser Tyr Glu Asn
                        20                  25                  30

Phe Met Gly Trp Tyr Arg Gln Ala Pro Gly Lys Glu Arg Glu Leu Val
                        35                  40                  45

Ala Gly Ile Asn Asp Gly Thr Asn Thr Tyr Tyr Ala Asp Ser Val Lys
                        50                  55                  60

Gly Arg Phe Thr Ile Ser Arg Asp Asn Ala Lys Asn Thr Val Tyr Leu
          65                          70                  75                  80

Gln Met Asn Ser Leu Lys Pro Glu Asp Thr Ala Val Tyr Tyr Cys Ala
                        85                  90                  95

Val Ile Gly Thr Ser Val Leu Gly His Ala Tyr Trp Gly Gln Gly Thr
                        100                 105                 110

Gln Val Thr Val Ser Ser Asp Lys Thr His Thr Cys Pro Pro Cys Pro
                        115                 120                 125

Ala Pro Glu Leu Leu Gly Gly Pro Ser Val Phe Leu Phe Pro Pro Lys
                        130                 135                 140

Pro Lys Asp Thr Leu Met Ile Ser Arg Thr Pro Glu Val Thr Cys Val
          145                         150                 155                 160

Val Val Asp Val Ser His Glu Asp Pro Glu Val Lys Phe Asn Trp Tyr
                        165                 170                 175

Val Asp Gly Val Glu Val His Asn Ala Lys Thr Lys Pro Arg Glu Glu
                        180                 185                 190

Gln Tyr Asn Ser Thr Tyr Arg Val Val Ser Val Leu Thr Val Leu His
                        195                 200                 205

Gln Asp Trp Leu Asn Gly Lys Glu Tyr Lys Cys Lys Val Ser Asn Lys
                        210                 215                 220

Ala Leu Pro Ala Pro Ile Glu Lys Thr Ile Ser Lys Ala Lys Gly Gln
          225                         230                 235                 240

Pro Arg Glu Pro Gln Val Tyr Thr Leu Pro Pro Ser Arg Glu Glu Met
```

```
            245                 250                 255
Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 46
<211> LENGTH: 345
<212> TYPE: PRT
<213> ORGANISM: Artificial Sequence
<220> FEATURE:
<223> OTHER INFORMATION: RBD1i1-Fc nanobody

<400> SEQUENCE: 46

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Glu Asn
            20                  25                  30

Phe Met Gly Trp Tyr Arg Gln Ala Pro Gly Lys Glu Arg Lys Leu Val
        35                  40                  45

Ala Gly Ile Asn Asp Gly Thr Asn Thr Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Ala
                85                  90                  95

Val Ile Gly Ala Ser Val Leu Gly His Ala Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
```

```
              260                 265                 270
Ser Asp Ile Ala Val Glu Trp Glu Ser Asn Gly Gln Pro Glu Asn Asn
        275                 280                 285

Tyr Lys Thr Thr Pro Val Leu Asp Ser Asp Gly Ser Phe Phe Leu
        290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
        340                 345

<210> SEQ ID NO 47
<211> LENGTH: 345
<212> TYPE: PRT
<213> ORGANISM: Artificial Sequence
<220> FEATURE:
<223> OTHER INFORMATION: RBD1i13-Fc nanobody

<400> SEQUENCE: 47

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Glu Asn
            20                  25                  30

Phe Met Gly Trp Tyr Arg Gln Ala Pro Gly Lys Gly Arg Lys Leu Val
        35                  40                  45

Ala Gly Ile Asn Asp Gly Thr Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Ala
                85                  90                  95

Val Ile Gly Ala Ser Val Leu Gly His Ala Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
```

```
            275                 280                 285
Tyr Lys Thr Thr Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
340                 345

<210> SEQ ID NO 48
<211> LENGTH: 345
<212> TYPE: PRT
<213> ORGANISM: Artificial Sequence
<220> FEATURE:
<223> OTHER INFORMATION: RBD3-Fc nanobody

<400> SEQUENCE: 48

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
                20                  25                  30

Phe Met Gly Trp Tyr Arg Gln Ala Pro Gly Lys Glu Arg Glu Leu Val
            35                  40                  45

Ala Ala Ile Gly Arg Gly Ser Asn Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asn Ala Thr Tyr Pro Tyr Tyr Val Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
```

```
                290                 295                 300
Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 49
<211> LENGTH: 345
<212> TYPE: PRT
<213> ORGANISM: Artificial Sequence
<220> FEATURE:
<223> OTHER INFORMATION: RBD3i2-Fc nanobody

<400> SEQUENCE: 49

Gln Ala Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
            20                  25                  30

Phe Met Gly Trp Tyr Arg Gln Ala Pro Gly Lys Glu Arg Glu Leu Val
        35                  40                  45

Ala Ala Ile Gly Arg Gly Ser Asn Thr Arg Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asn Ala Thr Tyr Pro Tyr Tyr Val Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
```

```
                305                 310                 315                 320
Phe Ser Cys Ser Val Met His Glu Ala Leu His Asn His Tyr Thr Gln
                325                 330                 335
Lys Ser Leu Ser Leu Ser Pro Gly Lys
            340                 345

<210> SEQ ID NO 50
<211> LENGTH: 345
<212> TYPE: PRT
<213> ORGANISM: Artificial Sequence
<220> FEATURE:
<223> OTHER INFORMATION: RBD3i17-Fc nanobody

<400> SEQUENCE: 50

Gln Ala Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asp Phe Arg
            20                  25                  30

Phe Met Gly Trp Tyr Arg Gln Ala Pro Gly Lys Glu Arg Glu Leu Val
            35                  40                  45

Ala Ala Ile Gly Arg Gly Ser Asn Thr Arg Cys Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Asn Ala Thr Tyr Pro Tyr Tyr Val Tyr Trp Gly Gln Gly Thr
            100                 105                 110

Gln Val Thr Val Ser Ser Asp Lys Thr His Thr Cys Pro Pro Cys Pro
            115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
```

<210> SEQ ID NO 51
<211> LENGTH: 349
<212> TYPE: PRT
<213> ORGANISM: Artificial Sequence
<220> FEATURE:
<223> OTHER INFORMATION: RBD6-Fc nanobody

<400> SEQUENCE: 51

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Thr Thr Tyr
            20                  25                  30

Leu Met Gly Trp Tyr Arg Gln Ala Pro Gly Lys Glu Arg Glu Phe Val
        35                  40                  45

Ala Thr Ile Asn Arg Gly Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Asp Tyr Gly Leu Ala Tyr His Arg Tyr Trp
            100                 105                 110

Gly Gln Gly Thr Gln Val Thr Val Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345
```

<210> SEQ ID NO 52
<211> LENGTH: 349
<212> TYPE: PRT
<213> ORGANISM: Artificial Sequence
<220> FEATURE:
<223> OTHER INFORMATION: RBD6id-Fc nanobody

<400> SEQUENCE: 52

Gln Val Gln Leu Gln Glu Ser Gly Gly Gly Leu Val Gln Ala Gly Gly
1               5                   10                  15

Ser Leu Arg Leu Asn Cys Ala Ala Asn Gly Ser Ile Ser Thr Thr Tyr
            20                  25                  30

Leu Met Gly Trp Tyr Arg Gln Ala Pro Gly Lys Glu Arg Glu Phe Val
        35                  40                  45

Ala Thr Ile Asn Arg Gly Gly Ser Thr Tyr Tyr Ala Ile Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Asp Tyr Gly Leu Ala Tyr His Arg Tyr Trp
            100                 105                 110

Gly Gln Gly Thr Gln Val Thr Val Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345

```
<210> SEQ ID NO 53
<211> LENGTH: 349
<212> TYPE: PRT
<213> ORGANISM: Artificial Sequence
<220> FEATURE:
<223> OTHER INFORMATION: RBD6i10-Fc nanobody

<400> SEQUENCE: 53
```

| | | | | | | | | | | | | | | | |
|---|---|---|---|---|---|---|---|---|---|---|---|---|---|---|---|
|Gln|Val|Gln|Leu|Gln|Glu|Ser|Gly|Gly|Gly|Leu|Val|Gln|Ala|Gly|Gly|
|1| | | |5| | | | |10| | | | |15| |
|Ser|Leu|Arg|Leu|Asn|Cys|Ala|Ala|Ser|Gly|Ser|Ile|Ser|Thr|Thr|Tyr|
| | | |20| | | | |25| | | | |30| | |
|Leu|Met|Gly|Trp|Tyr|Arg|Gln|Ala|Pro|Gly|Lys|Glu|Arg|Lys|Phe|Val|
| | |35| | | | |40| | | | |45| | | |
|Ala|Thr|Ile|Asn|Arg|Gly|Gly|Ser|Thr|Tyr|Tyr|Ala|Val|Ser|Val|Lys|
| |50| | | | |55| | | | |60| | | | |
|Gly|Arg|Phe|Thr|Ile|Ser|Arg|Asp|Asn|Ala|Lys|Asn|Thr|Val|Tyr|Leu|
|65| | | | |70| | | | |75| | | | |80|
|Gln|Met|Asn|Ser|Leu|Lys|Pro|Glu|Asp|Thr|Ala|Val|Tyr|Tyr|Cys|Ala|
| | | | |85| | | | |90| | | | |95| |
|Val|Gly|Trp|Pro|Asp|Pro|Asp|Tyr|Gly|Leu|Ala|Tyr|His|Arg|Tyr|Trp|
| | | |100| | | | |105| | | | |110| | |
|Gly|Gln|Gly|Thr|Gln|Val|Thr|Val|Asn|Ser|Asp|Lys|Thr|His|Thr|Cys|
| | |115| | | | |120| | | | |125| | | |
|Pro|Pro|Cys|Pro|Ala|Pro|Glu|Leu|Leu|Gly|Gly|Pro|Ser|Val|Phe|Leu|
| |130| | | | |135| | | | |140| | | | |
|Phe|Pro|Pro|Lys|Pro|Lys|Asp|Thr|Leu|Met|Ile|Ser|Arg|Thr|Pro|Glu|
|145| | | | |150| | | | |155| | | | |160|
|Val|Thr|Cys|Val|Val|Val|Asp|Val|Ser|His|Glu|Asp|Pro|Glu|Val|Lys|
| | | | |165| | | | |170| | | | |175| |
|Phe|Asn|Trp|Tyr|Val|Asp|Gly|Val|Glu|Val|His|Asn|Ala|Lys|Thr|Lys|
| | | |180| | | | |185| | | | |190| | |
|Pro|Arg|Glu|Glu|Gln|Tyr|Asn|Ser|Thr|Tyr|Arg|Val|Val|Ser|Val|Leu|
| | |195| | | | |200| | | | |205| | | |
|Thr|Val|Leu|His|Gln|Asp|Trp|Leu|Asn|Gly|Lys|Glu|Tyr|Lys|Cys|Lys|
| |210| | | | |215| | | | |220| | | | |
|Val|Ser|Asn|Lys|Ala|Leu|Pro|Ala|Pro|Ile|Glu|Lys|Thr|Ile|Ser|Lys|
|225| | | | |230| | | | |235| | | | |240|
|Ala|Lys|Gly|Gln|Pro|Arg|Glu|Pro|Gln|Val|Tyr|Thr|Leu|Pro|Pro|Ser|
| | | | |245| | | | |250| | | | |255| |
|Arg|Glu|Glu|Met|Thr|Lys|Asn|Gln|Val|Ser|Leu|Thr|Cys|Leu|Val|Lys|
| | | |260| | | | |265| | | | |270| | |
|Gly|Phe|Tyr|Pro|Ser|Asp|Ile|Ala|Val|Glu|Trp|Glu|Ser|Asn|Gly|Gln|
| | |275| | | | |280| | | | |285| | | |
|Pro|Glu|Asn|Asn|Tyr|Lys|Thr|Thr|Pro|Pro|Val|Leu|Asp|Ser|Asp|Gly|
| |290| | | | |295| | | | |300| | | | |
|Ser|Phe|Phe|Leu|Tyr|Ser|Lys|Leu|Thr|Val|Asp|Lys|Ser|Arg|Trp|Gln|
|305| | | | |310| | | | |315| | | | |320|
|Gln|Gly|Asn|Val|Phe|Ser|Cys|Ser|Val|Met|His|Glu|Ala|Leu|His|Asn|
| | | | |325| | | | |330| | | | |335| |
|His|Tyr|Thr|Gln|Lys|Ser|Leu|Ser|Leu|Ser|Pro|Gly|Lys| | | |
| | | |340| | | | |345| | | | | | | |

```
<210> SEQ ID NO 54
<211> LENGTH: 349
<212> TYPE: PRT
```

<213> ORGANISM: Artificial Sequence
<220> FEATURE:
<223> OTHER INFORMATION: RBD6i13-Fc nanobody

<400> SEQUENCE: 54

Gln Val Gln Leu Gln Glu Ser Gly Gly Gly Leu Val Gln Ala Gly Gly
1               5                   10                  15

Ser Leu Arg Leu Asn Cys Ala Ala Ser Gly Ser Ile Ser Thr Thr Tyr
            20                  25                  30

Leu Met Gly Trp Tyr Arg Gln Ala Pro Gly Lys Glu Arg Lys Phe Val
        35                  40                  45

Ala Thr Ile Asn Arg Gly Gly Ser Thr Tyr Tyr Ala Val Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Gly Trp Pro Asp Pro Gly Tyr Gly Leu Ala Tyr His Arg Tyr Trp
            100                 105                 110

Gly Gln Gly Thr Gln Val Thr Val Asn Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345

<210> SEQ ID NO 55
<211> LENGTH: 348
<212> TYPE: PRT
<213> ORGANISM: Artificial Sequence
<220> FEATURE:
<223> OTHER INFORMATION: RBD7-Fc nanobody

<400> SEQUENCE: 55

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Glu Phe Val
        35                  40                  45

Ala Gly Ile Gly Gly Ser Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Arg Gly Tyr Phe Ser Tyr Trp Gly
            100                 105                 110

Gln Gly Thr Gln Val Thr Val Ser Ser Asp Lys Thr His Thr Cys Pro
            115                 120                 125

Pro Cys Pro Ala Pro Glu Leu Leu Gly Gly Pro Ser Val Phe Leu Phe
        130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 56
<211> LENGTH: 348
<212> TYPE: PRT
<213> ORGANISM: Artificial Sequence
<220> FEATURE:
<223> OTHER INFORMATION: RBD7i12-Fc nanobody

<400> SEQUENCE: 56

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Glu Phe Val
        35                  40                  45

Ala Gly Ile Gly Gly Ser Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Cys Arg Gly Tyr Phe Ser Tyr Trp Gly
            100                 105                 110

Gln Gly Thr Gln Val Thr Val Ser Ser Asp Lys Thr His Thr Cys Pro
            115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 57
<211> LENGTH: 348
<212> TYPE: PRT
<213> ORGANISM: Artificial Sequence
<220> FEATURE:
<223> OTHER INFORMATION: RBD7i13-Fc nanobody

<400> SEQUENCE: 57

Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Tyr Ile Ser Gly Ala Tyr
            20                  25                  30

Tyr Met Gly Trp Tyr Arg Gln Ala Pro Gly Lys Glu Arg Lys Phe Val
            35                  40                  45

Ala Gly Ile Gly Gly Ser Thr Asn Tyr Ala Asp Ser Val Lys Gly
        50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Val
                85                  90                  95

Tyr Gln Ser Val Ala Tyr Tyr Cys Arg Gly Tyr Phe Ser Tyr Trp Gly
                100                 105                 110

Gln Gly Thr Gln Val Thr Val Ser Ser Asp Lys Thr His Thr Cys Pro
            115                 120                 125

Pro Cys Pro Ala Pro Glu Leu Leu Gly Gly Pro Ser Val Phe Leu Phe
        130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
                180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 58
<211> LENGTH: 353
<212> TYPE: PRT
<213> ORGANISM: Artificial Sequence
<220> FEATURE:
<223> OTHER INFORMATION: RBD10-Fc nanobody

<400> SEQUENCE: 58

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Met Gly Trp Tyr Arg Gln Ala Pro Gly Lys Glu Arg Glu Phe Val
            35                  40                  45

Ala Thr Ile Ala Asp Gly Ser Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser Asp Lys
            115                 120                 125

Thr His Thr Cys Pro Pro Cys Pro Ala Pro Glu Leu Leu Gly Gly Pro
            130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 59
<211> LENGTH: 353
<212> TYPE: PRT
<213> ORGANISM: Artificial Sequence
<220> FEATURE:
<223> OTHER INFORMATION: RBD10i10-Fc nanobody

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Met Gly Trp Tyr Arg Gln Ala Pro Gly Lys Gly Arg Lys Phe Val

```
                35                  40                  45

Ala Thr Ile Ala Asp Gly Gly Ser Thr Asn Tyr Ala Gly Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Leu Gly Gln Val Ser Glu Tyr Asn Ser Ala Ser Tyr Glu Trp Thr
                100                 105                 110

Tyr Pro Tyr Trp Gly Gln Gly Thr Gln Val Thr Val Ser Ser Asp Lys
            115                 120                 125

Thr His Thr Cys Pro Pro Cys Pro Ala Pro Glu Leu Leu Gly Gly Pro
130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 60
<211> LENGTH: 353
<212> TYPE: PRT
<213> ORGANISM: Artificial Sequence
<220> FEATURE:
<223> OTHER INFORMATION: RBD10i14-Fc nanobody

<400> SEQUENCE: 60

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Thr Ile Phe Gln Val Gly
            20                  25                  30

Ser Val Gly Trp Tyr Arg Gln Ala Pro Gly Lys Gly Arg Lys Phe Val
        35                  40                  45
```

Ala Thr Ile Ala Asp Gly Ser Thr Asn Tyr Ala Gly Ser Val Lys
             50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser Asp Lys
            115                 120                 125

Thr His Thr Cys Pro Pro Cys Pro Ala Pro Glu Leu Leu Gly Gly Pro
        130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 61
<211> LENGTH: 345
<212> TYPE: PRT
<213> ORGANISM: Artificial Sequence
<220> FEATURE:
<223> OTHER INFORMATION: RBD11-Fc nanobody

<400> SEQUENCE: 61

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Asn Ile Phe Ala Lys Val
                20                  25                  30

Trp Met Gly Trp Tyr Arg Gln Ala Pro Gly Lys Glu Arg Glu Phe Val
            35                  40                  45

```
Ala Ser Ile Ala Asn Gly Ala Thr Thr Tyr Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Arg Asn Trp Ser Gly Leu Gly His Phe Tyr Trp Gly Gln Gly Thr
            100                 105                 110

Gln Val Thr Val Ser Ser Asp Lys Thr His Thr Cys Pro Pro Cys Pro
            115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 62
<211> LENGTH: 345
<212> TYPE: PRT
<213> ORGANISM: Artificial Sequence
<220> FEATURE:
<223> OTHER INFORMATION: RBD11i12-Fc nanobody

<400> SEQUENCE: 62

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Ala Lys Val
            20                  25                  30

Trp Met Gly Trp Tyr Arg Gln Ala Pro Gly Lys Gly Arg Glu Phe Val
        35                  40                  45

Ala Ser Ile Ala Asn Gly Ala Thr Thr Tyr Tyr Ala Asp Ser Val Lys
    50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Arg Asn Trp Ser Gly Leu Gly Tyr Phe Tyr Trp Ser Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 63
<211> LENGTH: 115
<212> TYPE: PRT
<213> ORGANISM: Artificial Sequence
<220> FEATURE:
<223> OTHER INFORMATION: NbG1 nanobody

<400> SEQUENCE: 63

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Ser Ser Tyr
                20                  25                  30

Ala Met Gly Trp Tyr Arg Gln Ala Pro Gly Lys Glu Arg Glu Phe Val
            35                  40                  45

Ala Ala Ile Ser Trp Ser Gly Gly Ser Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80
```

```
Leu Gln Met Asn Ser Leu Lys Pro Glu Asp Thr Ala Val Tyr Tyr Cys
                85                  90                  95

Ala Arg His Trp Ser Ala Arg Tyr Trp Gly Gln Gly Thr Gln Val Thr
            100                 105                 110

Val Ser Ser
        115

<210> SEQ ID NO 64
<211> LENGTH: 115
<212> TYPE: PRT
<213> ORGANISM: Artificial Sequence
<220> FEATURE:
<223> OTHER INFORMATION: NbGli1 nanobody

<400> SEQUENCE: 64

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Ser Tyr
            20                  25                  30

Ala Met Gly Trp Tyr Arg Gln Ala Pro Gly Lys Glu Arg Glu Phe Val
            35                  40                  45

Ala Ala Ile Ser Trp Ser Gly Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Tyr
                85                  90                  95

Ala Arg His Trp Ser Ala Arg Tyr Trp Gly Gln Gly Thr Gln Val Thr
            100                 105                 110

Val Ser Ser
        115

<210> SEQ ID NO 65
<211> LENGTH: 127
<212> TYPE: PRT
<213> ORGANISM: Artificial Sequence
<220> FEATURE:
<223> OTHER INFORMATION: Sequence showing mutations in parental nanobody
      using prior art methods

<400> SEQUENCE: 65

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asp Val Asp
            20                  25                  30

Ile Met Gly Trp Tyr Arg Gln Ala Pro Gly Lys Glu Arg Glu Leu Val
            35                  40                  45

Ala Ser Ile Thr Asp Gly Gly Ser Thr Asp Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Val Ala Tyr Pro Asp Ile Pro Thr Tyr Phe Asp Tyr Asp Ser Asp
            100                 105                 110

Asn Phe Tyr Trp Gly Gln Gly Thr Gln Val Thr Val Ser Ser
            115                 120                 125
```

```
<210> SEQ ID NO 66
<211> LENGTH: 127
<212> TYPE: PRT
<213> ORGANISM: Artificial Sequence
<220> FEATURE:
<223> OTHER INFORMATION: Sequence showing mutations in parental nanobody
      using inventive method

<400> SEQUENCE: 66

Gln Val Gln Leu Gln Glu Ser Gly Gly Leu Val Gln Ala Gly Gly
1               5                   10                  15

Ser Leu Arg Leu Ser Cys Ala Ala Ser Gly Asn Ile Phe Asp Ala Asp
            20                  25                  30

Ile Met Gly Trp Tyr Arg Gln Ala Pro Gly Lys Glu Cys Glu Leu Val
            35                  40                  45

Ala Ser Ile Thr Asp Gly Gly Ser Thr Asn Tyr Ala Asp Ser Val Lys
        50                  55                  60

Gly His Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Val Ala Tyr Pro Asp Ile Pro Thr Tyr Phe Asp Tyr Asp Ser Asp
            100                 105                 110

His Phe Tyr Trp Gly Gln Gly Thr Gln Val Thr Val Ser Ser Ser
            115                 120                 125
```